US011814634B2

(12) United States Patent
Nakasone et al.

(10) Patent No.: US 11,814,634 B2
(45) Date of Patent: *Nov. 14, 2023

(54) TRANSFORMED PLANT AND FLOWERING REGULATION METHOD USING FLOWERING-INDUCING GENE

(71) Applicant: TOYOTA JIDOSHA KABUSHIKI KAISHA, Toyota (JP)

(72) Inventors: Akari Nakasone, Miyoshi (JP); Yasuyo Shimamoto, Nagakute (JP); Madoka Abe, Nagoya (JP); Satoshi Kondo, Miyoshi (JP); Sumire Fujiwara, Tsukuba (JP); Tomoko Niki, Tsukuba (JP); Kaoru Suzuki, Sapporo (JP); Nobutaka Mitsuda, Tsukuba (JP); Yoshimi Nakano, Tsukuba (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 126 days.

This patent is subject to a terminal disclaimer.

(21) Appl. No.: 17/481,836

(22) Filed: Sep. 22, 2021

(65) Prior Publication Data

US 2022/0064655 A1    Mar. 3, 2022

Related U.S. Application Data

(63) Continuation of application No. 16/807,650, filed on Mar. 3, 2020, now Pat. No. 11,214,814.

(30) Foreign Application Priority Data

Mar. 5, 2019  (JP) ................................ 2019-039843

(51) Int. Cl.
    *C12N 15/82*    (2006.01)
(52) U.S. Cl.
    CPC ................................. *C12N 15/827* (2013.01)
(58) Field of Classification Search
    None
    See application file for complete search history.

(56) References Cited

U.S. PATENT DOCUMENTS

| | | | |
|---|---|---|---|
| 6,225,530 B1 | 5/2001 | Weigel et al. | |
| 7,196,246 B2 | 3/2007 | Yano et al. | |
| 7,732,668 B2 | 6/2010 | Danilevskaya et al. | |
| 7,888,122 B2 | 2/2011 | Amasino et al. | |
| 8,785,724 B2 | 7/2014 | An et al. | |
| 9,512,441 B2 | 12/2016 | Nishimura et al. | |
| 11,214,814 B2 * | 1/2022 | Nakasone | C12N 15/827 |
| 2001/0049831 A1 * | 12/2001 | Weigel | C12N 15/8261 536/23.6 |
| 2011/0257013 A1 | 10/2011 | Saijo et al. | |
| 2012/0283102 A1 | 11/2012 | Matsumoto et al. | |
| 2013/0019345 A1 | 1/2013 | Ohki et al. | |
| 2016/0002648 A1 | 1/2016 | Guo et al. | |
| 2018/0057831 A1 | 3/2018 | Fromm | |

FOREIGN PATENT DOCUMENTS

| | | |
|---|---|---|
| JE | 2002-537768 A | 11/2002 |
| JP | 2000-139250 A | 5/2000 |
| JP | 2002-511270 A | 4/2002 |
| JP | 2002-153283 A | 5/2002 |
| JP | 2008-525013 A | 7/2008 |
| JP | 5679219 B2 | 3/2015 |
| JP | 5828302 B2 | 12/2015 |
| WO | 02/44390 A2 | 6/2002 |
| WO | 2006/127310 A2 | 11/2006 |
| WO | 2011/115222 A1 | 9/2011 |

OTHER PUBLICATIONS

Protein Flowering Locus T [*Sorghum bicolor*], NCBI Reference Sequence XP_002446704.1, NCBI Blast, Published Jun. 13, 2017. (Year: 2017).*
Pin, P. A., and Ove Nilsson. "The multifaceted roles of Flowering Locus T in plant development." Plant, cell & environment 35.10 (2012): 1742-1755. (Year: 2012).*
Igor Kardailsky, "Activation Tagging of the Floral Inducer FT," Dec. 1999, Science, vol. 286, pp. 1962-1965 (Year: 1999).
Non-final Office Action dated Nov. 2, 2020 in U.S. Appl. No. 16/807,650.
Final Office Action dated May 5, 2021 in U.S. Appl. No. 16/807,650.
Notice of Allowance dated Sep. 1, 2021 in U.S. Appl. No. 16/807,650.
Kardailshy I. et al., "Activiation Tagging of the Floral Inducer FT", Science (www.sciencemag.org), Dec. 3, 1999, vol. 286 (5446): pp. 1962-1965.
Kojima S. et al., "Hd3a, a Rice Ortholog of the *Arabidopsis* FT Gene, Promotes Transition to Flowering Downstream of Hd1 under Short-Day Conditions", Plant Cell Physiol., vol. 43(10): pp. 1096-1105 (2002).
BLAST Search (https://blast.ncbi.nlm.nih.gov/Blast.cgi) (Year: 2021). Protein Flowering Locus T (*Sorghum bicolor*) (https://www.ncbi.nlm.nih.gov/protein/XP_002454134.1?report=genbank&log$=protalign&blast_rank=1&RID=8NJ4FWY9016) (Year: 2017).
Turck, Regulation and Identity of Florigen: Flowering Locus T Moves Center Stage, Annual Review of Plant Biology, 2008 (Year: 2008).
Igor Kardalisky, Activation Tagging of the Floral Inducer FT, Dec. 1999, Science, vol. 286, pp. 1962-1965 (Year: 1999).

* cited by examiner

*Primary Examiner* — Russell Kallis
(74) *Attorney, Agent, or Firm* — Dinsmore & Shohl LLP

(57) ABSTRACT

Novel sugarcane-derived flowering-inducing genes each encoding a protein comprising the amino acid sequence of SEQ ID NO: 2 or 4 (the ScFT6 gene and the ScZCN16 gene), by which the flowering time is accelerated more slowly than conventionally known flowering-inducing genes, are provided.

6 Claims, 4 Drawing Sheets

Specification includes a Sequence Listing.

```
                    SEQUENCE LISTING

<160> NUMBER OF SEQ ID NOS: 36

<210> SEQ ID NO 1
<211> LENGTH: 525
<212> TYPE: DNA
<213> ORGANISM: Saccharum spontaneum L
<220> FEATURE:
<221> NAME/KEY: CDS
<222> LOCATION: (1)..(525)

<400> SEQUENCE: 1 atg tca agg gat cca cta gta gta gga cat gta gta ggt gac att ttg      48
Met Ser Arg Asp Pro Leu Val Val Gly His Val Val Gly Asp Ile Leu
1               5                  10                  15 gac cca ttt att aaa aca gcc tca ctt aag gtt ctg tac aac aac aag      96
Asp Pro Phe Ile Lys Thr Ala Ser Leu Lys Val Leu Tyr Asn Asn Lys
            20                  25                  30 gaa ctg acc aat ggt tct gag ctc aag cca tca cag gta gca aat gaa     144
Glu Leu Thr Asn Gly Ser Glu Leu Lys Pro Ser Gln Val Ala Asn Glu
        35                  40                  45 cca agg gtt gaa att tct ggg cgc gaa atg agg aac cta tac act ctg     192
Pro Arg Val Glu Ile Ser Gly Arg Glu Met Arg Asn Leu Tyr Thr Leu
    50                  55                  60 gtg atg gtg gat cca gac tcc cca agt cca agt aac cca aca aaa aga     240
Val Met Val Asp Pro Asp Ser Pro Ser Pro Ser Asn Pro Thr Lys Arg
65                  70                  75                  80 gaa tac ctt cat tgg ttg gtg aca gac atc ccg gaa tca gca aat act     288
Glu Tyr Leu His Trp Leu Val Thr Asp Ile Pro Glu Ser Ala Asn Thr
                85                  90                  95 agc tat gga aat gaa att gtc agc tat gaa aac cca aag cca act gct     336
Ser Tyr Gly Asn Glu Ile Val Ser Tyr Glu Asn Pro Lys Pro Thr Ala
            100                 105                 110 gga ata cat cgc ttt gtc ttt gta ctc ttc tgc cag tct gtc cag caa     384
Gly Ile His Arg Phe Val Phe Val Leu Phe Cys Gln Ser Val Gln Gln
        115                 120                 125 acc gtt tat gca cca gga tgg aga caa aat ttc aac aca aga gac ttt     432
Thr Val Tyr Ala Pro Gly Trp Arg Gln Asn Phe Asn Thr Arg Asp Phe
    130                 135                 140 tct gcg ctc tat aat ctt gga cct cct gta gct gca gtg ttc ttc aat     480
Ser Ala Leu Tyr Asn Leu Gly Pro Pro Val Ala Ala Val Phe Phe Asn
145                 150                 155                 160 tgt caa agg gag aat ggg tgt gga ggc aga cga tat att aga taa        525
Cys Gln Arg Glu Asn Gly Cys Gly Gly Arg Arg Tyr Ile Arg
                165                 170

<210> SEQ ID NO 2
<211> LENGTH: 174
<212> TYPE: PRT
<213> ORGANISM: Saccharum spontaneum L

<400> SEQUENCE: 2

Met Ser Arg Asp Pro Leu Val Val Gly His Val Val Gly Asp Ile Leu
1               5                  10                  15

Asp Pro Phe Ile Lys Thr Ala Ser Leu Lys Val Leu Tyr Asn Asn Lys
            20                  25                  30

Glu Leu Thr Asn Gly Ser Glu Leu Lys Pro Ser Gln Val Ala Asn Glu
        35                  40                  45

Pro Arg Val Glu Ile Ser Gly Arg Glu Met Arg Asn Leu Tyr Thr Leu
    50                  55                  60
```

```
Val Met Val Asp Pro Asp Ser Pro Ser Pro Ser Asn Pro Thr Lys Arg
 65                 70                  75                  80

Glu Tyr Leu His Trp Leu Val Thr Asp Ile Pro Glu Ser Ala Asn Thr
                85                  90                  95

Ser Tyr Gly Asn Glu Ile Val Ser Tyr Glu Asn Pro Lys Pro Thr Ala
            100                 105                 110

Gly Ile His Arg Phe Val Phe Val Leu Phe Cys Gln Ser Val Gln Gln
        115                 120                 125

Thr Val Tyr Ala Pro Gly Trp Arg Gln Asn Phe Asn Thr Arg Asp Phe
130                 135                 140

Ser Ala Leu Tyr Asn Leu Gly Pro Pro Val Ala Val Phe Phe Asn
145                 150                 155                 160

Cys Gln Arg Glu Asn Gly Cys Gly Gly Arg Arg Tyr Ile Arg
                165                 170

<210> SEQ ID NO 3
<211> LENGTH: 525
<212> TYPE: DNA
<213> ORGANISM: Saccharum spontaneum L
<220> FEATURE:
<221> NAME/KEY: CDS
<222> LOCATION: (1)..(525)

<400> SEQUENCE: 3 atg tca agt gac cca ctt gtt gta agc aaa gta gtt gga gat atc ttg       48
Met Ser Ser Asp Pro Leu Val Val Ser Lys Val Val Gly Asp Ile Leu
1               5                   10                  15 gat cca ttt atc aaa tca gca tca ttt aga gtc cta tac aac aat agg       96
Asp Pro Phe Ile Lys Ser Ala Ser Phe Arg Val Leu Tyr Asn Asn Arg
                20                  25                  30 gaa ctg act aat gga tct gag ctc aag cca tcg caa gta gcc aat gaa      144
Glu Leu Thr Asn Gly Ser Glu Leu Lys Pro Ser Gln Val Ala Asn Glu
            35                  40                  45 cca agg atc gag att gct gga cat gac atg agg acc ctt tac act ttg      192
Pro Arg Ile Glu Ile Ala Gly His Asp Met Arg Thr Leu Tyr Thr Leu
        50                  55                  60 gtg atg gtg gat ccc gac tca cca agt cca agc aat cca acg aaa aga      240
Val Met Val Asp Pro Asp Ser Pro Ser Pro Ser Asn Pro Thr Lys Arg
65                  70                  75                  80 gag tac ctt cac tgg ttg gtg aca gat att cca gaa tca aca aat gtg      288
Glu Tyr Leu His Trp Leu Val Thr Asp Ile Pro Glu Ser Thr Asn Val
                85                  90                  95 agc tat gga aat gag gta gta agc tat gaa agt cca aag cca agt gct      336
Ser Tyr Gly Asn Glu Val Val Ser Tyr Glu Ser Pro Lys Pro Ser Ala
            100                 105                 110 gga ata cat cgc ttc gtc ttt gtg cta ttc cgc caa tct gtc cgg caa      384
Gly Ile His Arg Phe Val Phe Val Leu Phe Arg Gln Ser Val Arg Gln
        115                 120                 125 act att tat gcg cca gga tgg agg caa aat ttc aac aca aaa gac ttc      432
Thr Ile Tyr Ala Pro Gly Trp Arg Gln Asn Phe Asn Thr Lys Asp Phe
130                 135                 140 tca gca ctc tat aat cta gga cca cct gtg gcc tca gtg ttc ttc aac      480
Ser Ala Leu Tyr Asn Leu Gly Pro Pro Val Ala Ser Val Phe Phe Asn
145                 150                 155                 160 tgc caa agg gag aat ggg tgc ggt ggc aga cga tat att aga tga          525
Cys Gln Arg Glu Asn Gly Cys Gly Gly Arg Arg Tyr Ile Arg
                165                 170

<210> SEQ ID NO 4
<211> LENGTH: 174
```

```
<212> TYPE: PRT
<213> ORGANISM: Saccharum spontaneum L

<400> SEQUENCE: 4

Met Ser Ser Asp Pro Leu Val Val Ser Lys Val Val Gly Asp Ile Leu
1               5                   10                  15

Asp Pro Phe Ile Lys Ser Ala Ser Phe Arg Val Leu Tyr Asn Asn Arg
            20                  25                  30

Glu Leu Thr Asn Gly Ser Glu Leu Lys Pro Ser Gln Val Ala Asn Glu
        35                  40                  45

Pro Arg Ile Glu Ile Ala Gly His Asp Met Arg Thr Leu Tyr Thr Leu
    50                  55                  60

Val Met Val Asp Pro Asp Ser Pro Ser Pro Ser Asn Pro Thr Lys Arg
65                  70                  75                  80

Glu Tyr Leu His Trp Leu Val Thr Asp Ile Pro Glu Ser Thr Asn Val
                85                  90                  95

Ser Tyr Gly Asn Glu Val Val Ser Tyr Glu Ser Pro Lys Pro Ser Ala
            100                 105                 110

Gly Ile His Arg Phe Val Phe Val Leu Phe Arg Gln Ser Val Arg Gln
        115                 120                 125

Thr Ile Tyr Ala Pro Gly Trp Arg Gln Asn Phe Asn Thr Lys Asp Phe
    130                 135                 140

Ser Ala Leu Tyr Asn Leu Gly Pro Pro Val Ala Ser Val Phe Phe Asn
145                 150                 155                 160

Cys Gln Arg Glu Asn Gly Cys Gly Gly Arg Arg Tyr Ile Arg
                165                 170

<210> SEQ ID NO 5
<211> LENGTH: 60
<212> TYPE: DNA
<213> ORGANISM: Artificial
<220> FEATURE:
<223> OTHER INFORMATION: Synthetic DNA

<400> SEQUENCE: 5
ggggacaagt ttgtacaaaa aagcaggctt catgtctata aatataagag accctcttat      60

<210> SEQ ID NO 6
<211> LENGTH: 60
<212> TYPE: DNA
<213> ORGANISM: Artificial
<220> FEATURE:
<223> OTHER INFORMATION: Synthetic DNA

<400> SEQUENCE: 6
ggggaccact ttgtacaaga aagctgggtt aagtcttctt cctccgcagc cactctccct      60

<210> SEQ ID NO 7
<211> LENGTH: 26
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
```

```
<222> LOCATION: (15)..(15)
<223> OTHER INFORMATION: n is inosine
<220> FEATURE:
<221> NAME/KEY: misc_feature
<222> LOCATION: (24)..(24)
<223> OTHER INFORMATION: n is inosine

<400> SEQUENCE: 7
ytnmgngart ayytncaytg gytngt                                           26

<210> SEQ ID NO 8
<211> LENGTH: 25
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (11)..(11)
<223> OTHER INFORMATION: n is inosine
<220> FEATURE:
<221> NAME/KEY: misc_feature
<222> LOCATION: (17)..(17)
<223> OTHER INFORMATION: n is inosine
<220> FEATURE:
<221> NAME/KEY: misc_feature
<222> LOCATION: (20)..(20)
<223> OTHER INFORMATION: n is inosine
<220> FEATURE:
<221> NAME/KEY: misc_feature
<222> LOCATION: (23)..(23)
<223> OTHER INFORMATION: n is inosine

<400> SEQUENCE: 8
traarttytg nckccanccn ggngc                                            25

<210> SEQ ID NO 9
<211> LENGTH: 23
<212> TYPE: DNA
<213> ORGANISM: Artificial
<220> FEATURE:
<223> OTHER INFORMATION: Synthetic DNA

<400> SEQUENCE: 9
cacccgtcgg tggcccatta ttg                                              23

<210> SEQ ID NO 10
<211> LENGTH: 22
<212> TYPE: DNA
<213> ORGANISM: Artificial
<220> FEATURE:
<223> OTHER INFORMATION: Synthetic DNA

<400> SEQUENCE: 10
tcttatttca cccggatcga gt                                               22

<210> SEQ ID NO 11
<211> LENGTH: 60
<212> TYPE: DNA
<213> ORGANISM: Artificial
<220> FEATURE:
<223> OTHER INFORMATION: Synthetic DNA

<400> SEQUENCE: 11
ggggacaagt ttgtacaaaa aagcaggctc catgtcagca accgatcctt tggtcatggc      60

<210> SEQ ID NO 12
<211> LENGTH: 60
<212> TYPE: DNA
```

```
<213> ORGANISM: Artificial
<220> FEATURE:
<223> OTHER INFORMATION: Synthetic DNA

<400> SEQUENCE: 12
ggggaccact tgtacaaga aagctgggtc ctactcttcc ctaaaccttc ttccacccga      60

<210> SEQ ID NO 13
<211> LENGTH: 60
<212> TYPE: DNA
<213> ORGANISM: Artificial
<220> FEATURE:
<223> OTHER INFORMATION: Synthetic DNA

<400> SEQUENCE: 13
ggggacaagt tgtacaaaa aagcaggctc catggccggc agcggcaggg aaagggagac      60

<210> SEQ ID NO 14
<211> LENGTH: 60
<212> TYPE: DNA
<213> ORGANISM: Artificial
<220> FEATURE:
<223> OTHER INFORMATION: Synthetic DNA

<400> SEQUENCE: 14
ggggaccact tgtacaaga aagctgggtc tcatgagtac atcctccttc ccccggagcc      60

<210> SEQ ID NO 15
<211> LENGTH: 60
<212> TYPE: DNA
<213> ORGANISM: Artificial
<220> FEATURE:
<223> OTHER INFORMATION: Synthetic DNA

<400> SEQUENCE: 15
ggggacaagt tgtacaaaa aagcaggctc catgttcaat atgtctaggg acccattggt      60

<210> SEQ ID NO 16
<211> LENGTH: 60
<212> TYPE: DNA
<213> ORGANISM: Artificial
<220> FEATURE:
<223> OTHER INFORMATION: Synthetic DNA

<400> SEQUENCE: 16
ggggaccact tgtacaaga aagctgggtc tcaccttatg taccttcttc caccacagcc      60

<210> SEQ ID NO 17
<211> LENGTH: 60
<212> TYPE: DNA
<213> ORGANISM: Artificial
<220> FEATURE:
<223> OTHER INFORMATION: Synthetic DNA

<400> SEQUENCE: 17
ggggacaagt tgtacaaaa aagcaggctc catgtctcag gtggaaccgt tggttctggt      60

<210> SEQ ID NO 18
<211> LENGTH: 60
<212> TYPE: DNA
<213> ORGANISM: Artificial
<220> FEATURE:
<223> OTHER INFORMATION: Synthetic DNA

<400> SEQUENCE: 18
ggggaccact tgtacaaga aagctgggtc ttacgaactt tcgggcctga accttctgcc      60
```

<210> SEQ ID NO 19
<211> LENGTH: 60
<212> TYPE: DNA
<213> ORGANISM: Artificial
<220> FEATURE:
<223> OTHER INFORMATION: Synthetic DNA

<400> SEQUENCE: 19
ggggacaagt ttgtacaaaa aagcaggctc catgtcaagt gacccacttg ttgtaagcaa    60

<210> SEQ ID NO 20
<211> LENGTH: 60
<212> TYPE: DNA
<213> ORGANISM: Artificial
<220> FEATURE:
<223> OTHER INFORMATION: Synthetic DNA

<400> SEQUENCE: 20
ggggaccact ttgtacaaga aagctgggtc tcatctaata tatcgtctgc caccgcaccc    60

<210> SEQ ID NO 21
<211> LENGTH: 28
<212> TYPE: DNA
<213> ORGANISM: Artificial
<220> FEATURE:
<223> OTHER INFORMATION: Synthetic DNA

<400> SEQUENCE: 21
cacccaaaat tagcagtctt gactaacc                                       28

<210> SEQ ID NO 22
<211> LENGTH: 21
<212> TYPE: DNA
<213> ORGANISM: Artificial
<220> FEATURE:
<223> OTHER INFORMATION: Synthetic DNA

<400> SEQUENCE: 22
gcacagtcag tgagatggta t                                              21

<210> SEQ ID NO 23
<211> LENGTH: 24
<212> TYPE: DNA
<213> ORGANISM: Artificial
<220> FEATURE:
<223> OTHER INFORMATION: Synthetic DNA

<400> SEQUENCE: 23
caccatgtca cgaggcaggg atcc                                           24

<210> SEQ ID NO 24
<211> LENGTH: 20
<212> TYPE: DNA
<213> ORGANISM: Artificial
<220> FEATURE:
<223> OTHER INFORMATION: Synthetic DNA

<400> SEQUENCE: 24
tactgccttg acgtcgatgt                                                20

<210> SEQ ID NO 25
<211> LENGTH: 21
<212> TYPE: DNA
<213> ORGANISM: Artificial
<220> FEATURE:

```
<223> OTHER INFORMATION: Synthetic DNA

<400> SEQUENCE: 25
cgacgtctgt cgagaagttt c                                              21

<210> SEQ ID NO 26
<211> LENGTH: 20
<212> TYPE: DNA
<213> ORGANISM: Artificial
<220> FEATURE:
<223> OTHER INFORMATION: Synthetic DNA

<400> SEQUENCE: 26
attccttgcg gtccgaatgg                                                20

<210> SEQ ID NO 27
<211> LENGTH: 586
<212> TYPE: DNA
<213> ORGANISM: Artificial
<220> FEATURE:
<223> OTHER INFORMATION: A coding region of AtFT having attB1 and attB2

<400> SEQUENCE: 27
ggggacaagt ttgtacaaaa aagcaggctt catgtctata aatataagag accctcttat     60
agtaagcaga gttgttggag acgttcttga tccgtttaat agatcaatca ctctaaaggt    120
tacttatggc caaagagagg tgactaatgg cttggatcta aggccttctc aggttcaaaa    180
caagccaaga gttgagattg gtggagaaga cctcaggaac ttctatactt tggttatggt    240
ggatccagat gttccaagtc ctagcaaccc tcacctccga gaatatctcc attggttggt    300
gactgatatc cctgctacaa ctggaacaac ctttggcaat gagattgtgt gttacgaaaa    360
tccaagtccc actgcaggaa ttcatcgtgt cgtgtttata ttgtttcgac agcttggcag    420
gcaaacagtg tatgcaccag gtggcgcca  gaacttcaac actcgcgagt tgctgagat     480 ctacaatctc ggccttcccg tggccgcagt tttctacaat tgtcagaggg agagtggctg    540
cggaggaaga agacttaacc cagctttctt gtacaaagtg gtcccc                   586

<210> SEQ ID NO 28
<211> LENGTH: 601
<212> TYPE: DNA
<213> ORGANISM: Artificial
<220> FEATURE:
<223> OTHER INFORMATION: A coding region of OsHd3a having attB1 and
      attB2

<400> SEQUENCE: 28
ggggacaagt ttgtacaaaa aagcaggctc catggccgga agtggcaggg acagggaccc     60
tcttgtggtt ggtagggttg tgggtgatgt gctggacgcg ttcgtccgga gcaccaacct    120
caaggtcacc tatggctcca agaccgtgtc caatggctgc gagctcaagc cgtccatggt    180
cacccaccag cctagggtcg aggtcggcgg caatgacatg aggacattct acaccccttgt   240 gatggtagac ccagatgcac caagcccaag tgaccctaac cttagggagt atctacattg    300
gttggtcact gatattcctg gtactactgc agcgtcattt gggcaagagg tgatgtgcta    360
cgagagccca aggccaacca tggggatcca ccggctggtg ttcgtgctgt tccagcagct    420
ggggcgtcag acagtgtacg cgcccgggtg gcgtcagaac ttcaacacca aggacttcgc    480
cgagctctac aacctcggct cgccggtcgc cgccgtctac ttcaactgcc agcgcgaggc    540
aggctccggc ggcaggaggg tctaccccta ggacccagct ttcttgtaca aagtggtccc    600
```

```
                                                                c      601

<210> SEQ ID NO 29
<211> LENGTH: 613
<212> TYPE: DNA
<213> ORGANISM: Artificial
<220> FEATURE:
<223> OTHER INFORMATION: A coding region of ScFT3 having cacc sequence

<400> SEQUENCE: 29
cacccgtcgg tggcccatta ttgctgggct ggccgtgatc gaccggcacg cagcagcgca      60
gcagcggcca tgcagcgcgg ggacccgctg gcggtggggc gcatcatcgg cgacgtggtg     120
gaccccttcg tgcgccgggt gccgctccgc gtcgcctacg ccgcgcgcga gatctccaac     180
ggctgcgagc tcaggccctc cgccatcgcc gaccagccgc gcgtcgaggt cggcggaccc     240
gacatgcgca ccttctacac cctcgtgatg gtggatcctg atgcgccaag ccccagcgat     300
cccaacctca gggagtacct gcactggctg gtcactgaca ttccggcgac gactggagtt     360
tcttttggga ctgaggttgt gtgctacgag agccacggc cggtgctggg aatccacagg      420
atagtgtttc tgctcttcca acagctcggc cggcagacgg tctacgcccc agggtggcgg     480
cagaacttca gcacccgtga cttcgccgag ctctacaacc tcggcttgcc ggtcgccgct     540
gtctacttca actgccaaag ggagtccgga actggtggga agaatgtg aactcgatcc       600
gggtgaaata aga                                                       613

<210> SEQ ID NO 30
<211> LENGTH: 589
<212> TYPE: DNA
<213> ORGANISM: Artificial
<220> FEATURE:
<223> OTHER INFORMATION: A coding region of ScZCN8 having attB1 and
      attB2

<400> SEQUENCE: 30
ggggacaagt ttgtacaaaa aagcaggctc catgtcagca accgatcctt tggtcatggc      60
tcatgtcata caggatgtgt tggatcccttt tacaacaacc attccactaa gaataacata   120
caacaatagg ctacttctgg caagtgctga gctaaagcca tctgcggttg caagtaaacc    180
acgagtcgat gtcggtggca atgacatgag ggctttctac accctggtac tgattgaccc    240
ggacgctcca agtccaagcc atccatcact aagggagtac ttgcactgga tggtgacaga    300
tattcctgaa acaactagtg tcaactttgg ccaagagcta gtattttatg agagaccgga    360
cccaagatct ggcatccaca ggctcgtatt tgtgctgttc cgtcaacttg caggggggac    420
agtttttgca ccagaaatgc gccaccactt caactgcaga gctttgcac ggcaatatca     480
cctcagcgtt gccactgcta catatttcaa ctgtcaaagg gaaggtggat cgggtggaag    540
aaggtttagg gaagagtagg acccagcttt cttgtacaaa gtggtcccc               589

<210> SEQ ID NO 31
<211> LENGTH: 601
<212> TYPE: DNA
<213> ORGANISM: Artificial
<220> FEATURE:
<223> OTHER INFORMATION: A coding region of ScFT4 having attB1 and attB2

<400> SEQUENCE: 31
ggggacaagt ttgtacaaaa aagcaggctc catggccggc agcggcaggg aaagggagac      60
gctggtggtt ggtagggtgg tgggcgacgt gctggacccc ttcgtccgga ccaccaacct    120
```

| | |
|---|---|
| cagggtcagc tacggcacca ggaccgtatc caacggctgc gagctcaagc cgtccatggt | 180 |
| ggtgaaccag cccagggtcg aggtcggggg acccgacatg aggaccttct acaccctcgt | 240 |
| gatggtcgac ccggatgctc cgagcccaag cgacccaaac cttagggagt atttgcactg | 300 |
| gctggtcacg gatattccgg gaactactgg ggcagcattt gggcaagagg tgatctgcta | 360 |
| cgagagccct cggccgacca tggggatcca ccgcttcgtg ctggtgctgt ccagcagct | 420 |
| ggtgcggcag acggtgtacg ccccggggtg gcgccagaac ttcaacacca gggacttcgc | 480 |
| cgagctctac aacctgggcc ctcccgtggc cgccgtctac ttcaactgcc agcgtgaggc | 540 |
| cggctccggg ggaaggagga tgtactcatg agacccagct tccttgtaca agtggtccc | 600 |
| c | 601 |

<210> SEQ ID NO 32
<211> LENGTH: 595
<212> TYPE: DNA
<213> ORGANISM: Artificial
<220> FEATURE:
<223> OTHER INFORMATION: A coding region of ScFT5 having attB1 and attB2

<400> SEQUENCE: 32

| | |
|---|---|
| ggggacaagt ttgtacaaaa aagcaggctc catgttcaat atgtctaggg acccattggt | 60 |
| cgtcgggcat gttgtggggg atattgtgga tcccttcatc acaactgcgt cactgagggt | 120 |
| gttctacaac aataaggaga tgacaaatgg ttctgagctt aagccatctc aagtaatgaa | 180 |
| tgagccaagg gtccacatca gtgggcgtga catgaggact ctctacacac ttgtcatggt | 240 |
| ggacccagat gcaccaagcc ccagtaaccc tactaaaaga gagaaccttc actggttggt | 300 |
| gacagacatt ccagagacaa ctgatgccag cttcgggaat gagatagttc cttatgagag | 360 |
| cccacgtcca actgccggaa tccatcgctt tgcattcgtc ttgttcaggc agtcagtcag | 420 |
| gcagactacc tatgcgccgg ggtggagatc aaactttaac accagggact cgcagccat | 480 |
| ctacaacctt ggctcccctg tcgctgcagt gtacttcaac tgccagagag agaacggctg | 540 |
| tggtggaaga aggtacataa ggtgagaccc agctttcttg tacaaagtgg tcccc | 595 |

<210> SEQ ID NO 33
<211> LENGTH: 595
<212> TYPE: DNA
<213> ORGANISM: Artificial
<220> FEATURE:
<223> OTHER INFORMATION: A coding region of ScZCN12 having attB1 and
    attB2

<400> SEQUENCE: 33

| | |
|---|---|
| ggggacaagt ttgtacaaaa aagcaggctc catgtctcag gtggaaccgt tggttctggt | 60 |
| tcatgtgata cgagatgtgt tggattcatt tacaccaact ataccctca gaataaccta | 120 |
| caacaatagg ctacttctag caggtgttga gctgaagcca tccgcagtgg tgaataagcc | 180 |
| aagagttgat gttgggggca ccgacctcag ggtgttcttt acactggtat tagttgatcc | 240 |
| agatgcccca agcccaagca atccatcact gagggaatat ttgcactgga tggtgataga | 300 |
| tattccagga acaactgcag ccaactttgg tcaggagctc atgttttacg aaaggccaga | 360 |
| accgagatct ggtatacacc gcatggtatt tgtgctgttc cggcaacttg taggggggac | 420 |
| agttttttgca ccagacatgc gacataactt caactgcaag aactttgcac gtcagtacca | 480 |
| cctggacatt gtggctgcca catatttcaa ctgtcagagg gaagcaggat ctggggggcag | 540 |
| aaggttcagg cccgaaagtt cgtaagaccc agctttcttg tacaaagtgg tcccc | 595 |

<210> SEQ ID NO 34
<211> LENGTH: 586
<212> TYPE: DNA
<213> ORGANISM: Artificial
<220> FEATURE:
<223> OTHER INFORMATION: A coding region of ScZCN16 having attB1 and attB2

<400> SEQUENCE: 34

| | | | | | |
|---|---|---|---|---|---|
| ggggacaagt | tgtacaaaa | aagcaggctc | catgtcaagt | gacccacttg | ttgtaagcaa | 60 |
| agtagttgga | gatatcttgg | atccatttat | caaatcagca | tcatttagag | tcctatacaa | 120 |
| caatagggaa | ctgactaatg | gatctgagct | caagccatcg | caagtagcca | atgaaccaag | 180 |
| gatcgagatt | gctggacatg | acatgaggac | cctttacact | ttggtgatgg | tggatcccga | 240 |
| ctcaccaagt | ccaagcaatc | caacgaaaag | agagtacctt | cactggttgg | tgacagatat | 300 |
| tccagaatca | acaaatgtga | gctatggaaa | tgaggtagta | agctatgaaa | gtccaaagcc | 360 |
| aagtgctgga | atacatcgct | tcgtctttgt | gctattccgc | caatctgtcc | ggcaaactat | 420 |
| ttatgcgcca | ggatggaggc | aaaatttcaa | cacaaaagac | ttctcagcac | tctataatct | 480 |
| aggaccacct | gtggcctcag | tgttcttcaa | ctgccaaagg | gagaatgggt | gcggtggcag | 540 |
| acgatatatt | agatgagacc | cagctttctt | gtacaaagtg | gtcccc | | 586 |

<210> SEQ ID NO 35
<211> LENGTH: 574
<212> TYPE: DNA
<213> ORGANISM: Artificial
<220> FEATURE:
<223> OTHER INFORMATION: A coding region of ScFT6 having cacc sequence

<400> SEQUENCE: 35

| | | | | | |
|---|---|---|---|---|---|
| cacccaaaat | tagcagtctt | gactaaccat | gtcaagggat | ccactagtag | taggacatgt | 60 |
| agtaggtgac | attttggacc | catttattaa | aacagcctca | cttaaggttc | tgtacaacaa | 120 |
| caaggaactg | accaatggtt | ctgagctcaa | gccatcacag | gtagcaaatg | aaccaagggt | 180 |
| tgaaatttct | gggcgcgaaa | tgaggaacct | atacactctg | gtgatggtgg | atccagactc | 240 |
| cccaagtcca | agtaacccaa | caaaaagaga | ataccttcat | tggttggtga | cagacatccc | 300 |
| ggaatcagca | atactagct | atggaaatga | aattgtcagc | tatgaaaacc | caaagccaac | 360 |
| tgctggaata | catcgctttg | tctttgtact | cttctgccag | tctgtccagc | aaaccgttta | 420 |
| tgcaccagga | tggagacaaa | atttcaacac | aagagacttt | tctgcgctct | ataatcttgg | 480 |
| acctcctgta | gctgcagtgt | tcttcaattg | tcaagggag | aatgggtgtg | gaggcagacg | 540 |
| atatattaga | taaataccat | ctcactgact | gtgc | | | 574 |

<210> SEQ ID NO 36
<211> LENGTH: 578
<212> TYPE: DNA
<213> ORGANISM: Artificial
<220> FEATURE:
<223> OTHER INFORMATION: A coding region of ScFT7 having cacc sequence

<400> SEQUENCE: 36

| | | | | | |
|---|---|---|---|---|---|
| caccatgtca | cgaggcaggg | atcctttggc | attgagccag | gtaattggtg | atgtgttgga | 60 |
| tcccttcata | aagtcagcaa | caatgaggat | taattatggt | gacaaggaga | tcacaaatgg | 120 |
| cactggacta | cgagcgtctg | ctgtgctcaa | tgcaccacat | gttgagattg | aaggccacga | 180 |
| ccaaacaaag | ctctacacac | ttgttatggt | ggatcctgat | gcaccaagtc | caagtaaacc | 240 |

-continued

```
agagcacagg gaatatctgc attggttggt gacagacata ccagaggcaa gagacataca      300
ttttggcaat gaaatagttc cctatgaaag cccgaggcca ccagctggaa ttcatcgaat      360 tgttttgtg  ctattcaaac agcaagtaag acaaacagtt tatgcaccag gatggcggca      420
aaatttcaac atcagagact tctcagctat ttacaatctt ggagcaccag ttgctgcatt      480
atacttcaac tgccaaaagg aaagcggtgt tggtggcaga aggttcctgg gatcaagctg      540
aagaacagat acagagaaac atcgacgtca aggcagta                              578
```

TRANSFORMED PLANT AND FLOWERING REGULATION METHOD USING FLOWERING-INDUCING GENE

CROSS REFERENCE TO RELATED APPLICATIONS

The present application is a continuation of U.S. patent application Ser. No. 16/807,650, filed Mar. 3, 2020, which claims priority from Japanese patent application JP 2019-039843, filed Mar. 5, 2019, the contents of which are hereby incorporated by reference into this application.

SEQUENCE LISTING

The instant application contains a Sequence Listing which has been submitted in ASCII format via EFS-Web and is hereby incorporated by reference in its entirety. Said ASCII copy, created on Oct. 25, 2021 is named 08TMCL11103VA_SEQ.txt and is 24 KB is size.

BACKGROUND

Technical Field

The present disclosure relates to a transformed plant that has acquired improved properties by introducing a certain flowering-inducing gene there into and a flowering regulation method using the flowering-inducing gene.

Background Art

Conventionally, cross breeding of plants has been carried out with a combination based on experience and intuition, and a large number of progeny lines has been selected by comprehensive evaluation. Usually, in order to carry out crossing, it is necessary to go through a process of flowering induction, blooming/pollination, and seed setting promotion/seed harvesting. Depending on the plant type, this process can be scheduled only once a year, even in an area suitable for cultivation. Therefore, it took a very long time to develop one cultivar. Furthermore, when the cultivar to be bred was a cultivar that is difficult to flower or when the cultivars to be bred did not match in terms of time of blooming, it was very difficult to carry out desired crossing.

As explained above, in cross breeding, it was desired to develop a technology that would speed up the time of blooming by controlling the blooming of plants. It has been reported that it was possible to induce flowering (heading) of *Arabidopsis thaliana* or rice by causing a flowering-inducing gene such as the FT gene (AtFT gene) or the Hd3a gene (OsHd3a gene) to be overexpressed (JP 2000-139250 A, JP 2002-511270 A, and JP 2002-153283 A; Kardailsky I. et al., Science. 1999 Dec. 3; 286(5446):1962-5 and Kojima S. et al., Plant Cell Physiol 2002 October; 43(10):1096-105).

Meanwhile, in the case of using these flowering-inducing genes, as the genes have very powerful ability to induce flowering, flowering occurs at a stage when a plant is still small, and thus, the amount of seeds that can be harvested decreases, which has been problematic. JP 2008-525013 A and JP 2002-537768 A disclose a technology that controls the flowering time using a gene encoding a regulatory factor for controlling the expression of the flowering-inducing gene. However, as the technology disclosed in JP 2008-525013 A and JP 2002-537768 A causes the introduced regulatory factor to affect genes other than the flowering-inducing gene, undesirable characteristics may be imparted.

In addition, JP Patent No. 5828302 discloses a technology related to sugarcane into which the rice flowering-inducing gene Hd3a has been introduced to change the flowering time. However, even the technology disclosed in JP Patent No. 5828302 is also problematic because as the gene has very powerful ability to induce flowering, flowering occurs at a stage when a plant is still small.

Further, US2018/0057831 A1 discloses a technology that regulates the flowering time by allowing the expression of a flowering-inducing gene downstream of an alcohol-induced promoter. However, according to the technology disclosed in US2018/0057831 A1, the promoter needs to be activated with the aid of alcohol, which causes a problem that flowering regulation is time- and cost-consuming. Furthermore, WO2011/115222 A1 discloses a technology that regulates the flowering time by introducing a mutation into a certain site of the protein encoded by the Hd3a gene of rice. However, according to the technology disclosed in WO2011/115222 A1, there is a problem that production of such mutation gene is time- and cost-consuming. Moreover, US2011/0257013 A1 discloses a technology that regulates the flowering time by allowing the expression of a flowering-inducing gene downstream of a copper ion-inducible promoter. However, according to the technology disclosed in US2011/0257013 A1, the promoter needs to be activated with the aid of the copper ion-inducible promoter, which causes a problem that flowering regulation is time- and cost-consuming.

SUMMARY

As described above, flowering of a plant cannot be regulated at the desired time even by simply introducing a flowering-inducing gene into the plant. The flowering time can be regulated only by a method using an inducible promoter for regulating the expression of a flowering-inducing gene or utilizing a mutant-type flowering-inducing gene, which has been problematic.

In consideration of the above-described circumstances, the present disclosure provides a transformed plant having a novel flowering-inducing gene introduced thereinto, the gene having ability to induce flowering so as to function for accelerating the flowering time more slowly than conventionally known flowering-inducing genes, and a flowering regulation method using the flowering-inducing gene.

For example, introducing a certain flowering-inducing gene makes it possible to induce flowering more slowly than when a conventionally known flowering-inducing gene is introduced.

(1) A transformed plant or transformed plant cell, wherein a flowering-inducing gene encoding any one of the following proteins (a) to (c) has been introduced thereinto or wherein an expression of the flowering-inducing gene present as an endogenous gene has been enhanced.

(a) a protein comprising the amino acid sequence of SEQ ID NO: 2 or 4;

(b) a protein comprising an amino acid sequence having 90% or more identity to the amino acid sequence of SEQ ID NO: 2 or 4 and having ability to induce flowering; and (c) a protein comprising an amino acid sequence encoded by a polynucleotide capable of hybridizing with all or part of a polynucleotide comprising the nucleotide sequence of SEQ ID NO: 1 or 3 under stringent conditions and having ability to induce flowering.

(2) The transformed plant or transformed plant cell according to (1), which belongs to the family Poaceae.
(3) The transformed plant or transformed plant cell according to (1), which belongs to the genus *Saccharum*, *Erianthus*, *Sorghum*, or *Miscanthus*.
(4) A flowering induction method, comprising introducing a flowering-inducing gene encoding any one of the following proteins (a) to (c) or enhancing the expression of the flowering-inducing gene present as an endogenous gene:
(a) a protein comprising the amino acid sequence of SEQ ID NO: 2 or 4;
(b) a protein comprising an amino acid sequence having 90% or more identity to the amino acid sequence of SEQ ID NO: 2 or 4 and having ability to induce flowering; and
(c) a protein comprising an amino acid sequence encoded by a polynucleotide capable of hybridizing with all or part of a polynucleotide comprising the nucleotide sequence of SEQ ID NO: 1 or 3 under stringent conditions and having ability to induce flowering.
(5) The flowering induction method according to (4), which comprises introducing the flowering-inducing gene into a plant belonging to the family Poaceae.
(6) The flowering induction method according to (4), which comprises introducing the flowering-inducing gene into a plant belonging to the genus *Saccharum*, *Erianthus*, *Sorghum*, or *Miscanthus*.

According to the present disclosure, using a novel flowering-inducing gene makes it possible to promote flowering more slowly than when a conventionally known flowering-inducing gene is introduced. Therefore, in the case of the transformed plant or transformed plant cell according to the present disclosure, flowering induction occurs at a stage when a plant has grown more largely than when a conventionally known flowering-inducing gene is introduced. Accordingly, the transformed plant or transformed plant cell according to the present disclosure has an improved feature that the flowering time is accelerated while ensuring a sufficient seed yield.

DETAILED DESCRIPTION

Figure 1:
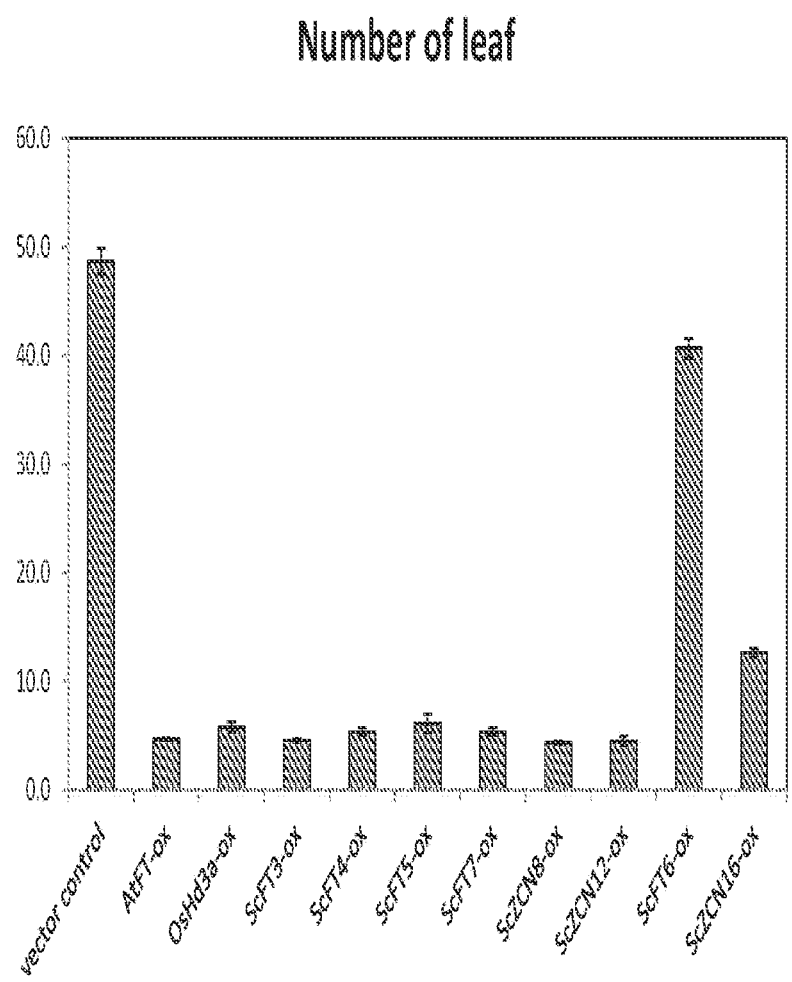
FIG. 1 is a characteristic diagram showing the results of investigating flower bud formation when transformed plants prepared by separately introducing FT family genes into the FT function-deficient strain were cultivated under long-day conditions.

The present disclosure will be described in detail below.
According to the present disclosure, a certain flowering-inducing gene is introduced into a plant cell to serve as a host or an expression of the flowering-inducing gene present as an endogenous gene is enhanced. Accordingly, flowering induction occurs in a transformed plant having the flowering-inducing gene introduced thereinto or showing enhanced expression of the flowering-inducing gene earlier than flowering induction in a wild-type plant not introducing the flowering-inducing gene or not showing the enhanced expression of the gene. Meanwhile, flowering induction occurs in the transformed plant later than flowering induction in a transformed plant having a conventionally known flowering-inducing gene introduced thereinto or showing enhanced expression of the conventionally known flowering-inducing gene present as an endogenous gene. In the following explanation, a phenomenon in which flowering induction occurs earlier than flowering induction in a wild-type plant, but later than flowering induction in a transformed plant having a conventionally known flowering-inducing gene introduced thereinto or showing enhanced expression of the conventionally known flowering-inducing gene present as an endogenous gene is expressed as, for example, "slow flowering induction" or "flowering induction occurs slowly."

The term "flowering induction" used herein refers to transition from the vegetative growth phase to the reproductive growth phase, which means formation, differentiation, and development of flower buds that occur before blooming. In addition, flowering is induced as a result of increased expression of various related genes caused by the formation of a complex of a florigen transported to the shoot apex through the vascular phloem. Therefore, the flowering induction time can also be judged by observing the formation, differentiation, and development of flower buds, by detecting the presence of a florigen or a florigen activation complex, or by detecting the transcript of a gene which is increasingly expressed by the florigen activation complex.

Flowering-Inducing Genes Involved in Slow Flowering Induction

The flowering-inducing gene involved in slow flowering induction according to the present disclosure is a gene encoding a protein comprising the amino acid sequence of SEQ ID NO: 2 or 4. Genes each encoding a protein comprising the amino acid sequence of SEQ ID NO: 2 or 4 are genes that have been newly identified from sugarcane based on sequence information on conventionally known flowering-inducing genes (the *Arabidopsis thaliana*-derived FT gene (AtFT gene), the rice-derived florigen gene (Hd3a gene), and the corn-derived florigen gene (ZCN8 gene)) explained in the Examples described later. Note that the flowering-inducing gene has, as a coding region, the nucleotide sequence of SEQ ID NO: 1 encoding the amino acid sequence of SEQ ID NO: 2 or the nucleotide sequence of SEQ ID NO: 3 encoding the amino acid sequence of SEQ ID NO: 4.

In the Examples described later, the flowering-inducing gene identified with the nucleotide sequence of SEQ ID NO: 1 and the amino acid sequence of SEQ ID NO: 2 is referred to as "ScFT6 gene" and the flowering-inducing gene identified with the nucleotide sequence of SEQ ID NO: 3 and the amino acid sequence of SEQ ID NO: 4 is referred to as "ScZCN16 gene."

In addition, examples of the flowering-inducing gene involved in slow flowering induction according to the present disclosure include genes homologous to the gene encoding the protein of SEQ ID NO: 2 or 4. These homologous genes include both genes that have evolved and branched from a common ancestor gene and genes that simply have similar nucleotide sequences, unlike the evolved and branched genes. Genes that have evolved and branched from a common ancestor gene include homologous genes (orthologs) of two different species and homologous genes (paralogs) that are generated within one species due to duplication. Genes homologous to the above-described flowering-inducing gene can be readily searched for or identified based on the amino acid sequence of SEQ ID NO: 2 or 4 using a known database such as GenBank.

Further, the flowering-inducing gene involved in slow flowering induction according to the present disclosure is not limited to a gene encoding a protein comprising the amino acid sequence of SEQ ID NO: 2 or 4 and may be a gene encoding a protein comprising an amino acid sequence having 80% or more identity, 85% or more identity in some embodiments, 90% or more identity in some other embodiments, 95% or more identity in still some other embodiments, and 98% or more identity in yet some other embodiments to the amino acid sequence of SEQ ID NO: 2 or 4. Note that a protein having an amino acid sequence that is different from the amino acid sequence of SEQ ID NO: 2 or 4 functions to cause slow flowering induction when it is expressed in a host plant. Here, the value of identity is a value obtained with default settings using a computer program implemented with the BLAST (Basic Local Alignment Search Tool) program and a database storing gene sequence information Furthermore, the flowering-inducing gene involved in slow flowering induction according to the present disclosure is not limited to a gene encoding a protein comprising the amino acid sequence of SEQ ID NO: 2 or 4 and may be a gene encoding a protein comprising an amino acid sequence in which one or more amino acids are deleted, substituted, added, or inserted in the amino acid sequence of SEQ ID NO: 2 or 4 and functioning to cause slow flowering induction. Here, the expression "one or more amino acids" means, for example, 1 to 20 amino acids, 1 to 10 amino acids in some embodiments, 1 to 7 amino acids in some other embodiments, 1 to 5 amino acids in still some other embodiments, and 1 to 3 amino acids in some particular embodiments. Amino acids can be deleted, substituted, or added by modifying a nucleotide sequence encoding a protein comprising the amino acid sequence of SEQ ID NO: 2 or 4 by a technique known in the art. A mutation can be introduced into a nucleotide sequence by a known method such as the Kunkel method or the Gapped duplex method or a method similar to such method. A mutation is introduced using, for example, a mutagenesis kit (e.g., Mutant-K or Mutant-G (trade name, TAKARA Bio Inc.)) or an LA PCR in vitro Mutagenesis series kit (trade name, TAKARA Bio Inc.) by the site-directed mutagenesis method. Mutagenesis may be carried out by a method using a chemical mutation agent such as EMS (ethyl methanesulfonic acid), 5-bromouracil, 2-aminopurine, hydroxylamine, N-methyl-N'-nitro-N-nitrosoguanidine, and a different carcinogenic compound or a method involving radiation treatment or ultraviolet treatment typically with X-ray, alpha ray, beta ray, gamma ray, or ion beam.

Moreover, the flowering-inducing gene involved in slow flowering induction according to the present disclosure may be a gene encoding a protein hybridizing with all or part of a complementary strand of DNA comprising the nucleotide sequence of SEQ ID NO: 1 or 3 under stringent conditions and functioning to cause slow flowering induction. The term "stringent conditions" used herein refers to conditions under which so-called specific hybrids are formed while non-specific hybrids are not formed. For example, such conditions include hybridization at 45° C. with 6×SSC (sodium chloride/sodium citrate) and subsequent washing at 50° C. to 65° C. with 0.2 to 1×SSC and 0.1% SDS or hybridization at 65° C. to 70° C. with 1×SSC and subsequent washing at 65° C. to 70° C. with 0.3×SSC. Hybridization can be carried out by a conventionally known method such as the method described in J. Sambrook et al. Molecular Cloning, A Laboratory Manual, 2nd Ed., Cold Spring Harbor Laboratory (1989).

Expression Vector

An expression vector is constructed such that it includes a nucleic acid having a promoter nucleotide sequence that enables constitutive expression and the above-described flowering-inducing gene. It is possible to produce a transformed plant having the flowering-inducing gene introduced thereinto with the use of the expression vector. In addition, an expression vector may be one that substitutes an endogenous promoter for regulating the expression of the flowering-inducing gene with a powerful promoter by homologous recombination in order to enhance the expression of the flowering-inducing gene present as an endogenous gene. In this case, an expression vector is constructed such that it has a powerful promoter described in detail later and a region necessary for homologous recombination.

Various conventionally known vectors can be used herein as a base vector for the expression vector. For example, a plasmid, phage, cosmid, or the like can be used, and a vector can be appropriately selected according to a plant cell into which the vector is introduced and a method for introducing the vector. Specific examples of such vector include pBI vectors such as pBR322, pBR325, pUC19, pUC119, pBluescript, and pBluescriptSK. In particular, in a case in which the method for introducing the vector into a plant cell uses *Agrobacterium*, a pBI binary vector is used in some embodiments. Specific examples of a pBI binary vector include pBIG, pBIN19, pBI101, pBI121, and pBI221.

The promoter is not particularly limited as long as it is a promoter that allows the flowering-inducing gene to be expressed in a plant, and a known promoter can be used as appropriate. Examples of such promoter include a cauliflower mosaic virus 35S promoter (CaMV35S), various actin gene promoters, various ubiquitin gene promoters, a nopaline synthase gene promoter, a tobacco PR1a gene promoter, a tomato ribulose 1,5-bisphosphate carboxylase/oxidase small subunit gene promoter, a napin gene promoter, and an oleosin gene promoter. Of these, a cauliflower mosaic virus 35S promoter, an actin gene promoter, or an ubiquitin gene promoter is used in some embodiments. The use of each of the above-described promoters allows an arbitrary gene to be strongly expressed when the gene is introduced into a plant cell.

In addition, a promoter that functions to allow a nucleic acid to be expressed in a plant in a site-specific manner can also be used. Any conventionally known promoter can be used as such promoter. By introducing the flowering-inducing gene in a site-specific manner using such promoter, it is possible to induce the expression of the gene in a plant organ or plant tissue formed with cells having the flowering-inducing gene introduced thereinto so as to cause slow flowering induction.

The expression vector may further include a nucleic acid having a different segment sequence, in addition to a promoter and the flowering-inducing gene. The nucleic acid having a different segment sequence is not particularly limited. Examples thereof include a nucleic acid having a terminator nucleotide sequence, a nucleic acid having a transformant selection marker nucleotide sequence, a nucleic acid having an enhancer nucleotide sequence, and a nucleic acid having a nucleotide sequence for improving translation efficiency. In addition, the recombinant expression vector may further have a T-DNA region. A T-DNA region can improve the efficiency of nucleic acid introduction especially when introducing a nucleic acid having a nucleotide sequence in the recombinant expression vector into a plant cell using *Agrobacterium*.

The nucleic acid having a terminator nucleotide sequence is not particularly limited as long as it functions as a transcription termination site, and it may be a known nucleic acid. For example, specific examples of such nucleic acid that can be used include the transcription termination site of the nopaline synthase gene (Nos terminator) and the transcription termination site of cauliflower mosaic virus 35S (CaMV35S terminator). Of these, the Nos terminator is used in some embodiments. The above-described recombinant vector can be prevented from causing an event of, for example, synthesizing an unnecessarily long transcript after being introduced into a plant cell by placing the terminator at an appropriate site.

Examples of the nucleic acid having a transformant selection marker nucleotide sequence that can be used include nucleic acids having drug-resistant genes. Specific examples of such drug-resistant genes include drug resistant genes against, for example, hygromycin, bleomycin, kanamycin, gentamicin, and chloramphenicol. Accordingly, by selecting a plant that grows in a medium containing such antibiotics, a transformed plant can be readily selected.

Examples of the nucleic acid having a nucleotide sequence for improving translation efficiency include a nucleic acid having the tobacco mosaic virus-derived omega sequence. The expression efficiency of the above-described flowering-inducing gene can be increased by placing this omega sequence-containing nucleic acid in the untranslated region (5'UTR) upstream of the protein coding region. Thus, the above-described recombinant expression vector can contain nucleic acids having various DNA segment sequences depending on the purpose.

The method for constructing a recombinant expression vector is also not particularly limited. A nucleic acid having the above-described promoter nucleotide sequence, the above-described flowering-inducing gene, and if needed, a nucleic acid having the above-described other DNA segment sequences can be inserted into an appropriately selected vector to serve as a base in a certain order. For example, the flowering-inducing gene and a nucleic acid having a promoter nucleotide sequence (and if needed, for example, a nucleic acid having a terminator nucleotide sequence) are ligated, thereby inserting the ligation product into the vector.

In addition, a method for propagating (producing) the expression vector is also not particularly limited, and a conventionally known method can be used. Usually, the vector can be propagated in *Escherichia coli* used as a host. At such time, the type of *Escherichia coli* may be selected depending on the vector type in some embodiments.

Transformation

The expression vector is introduced into a plant cell of interest by an ordinary transformation method. The method for introducing the expression vector into a plant cell (transformation method) is not particularly limited, and an appropriate conventionally known method can be used depending on the plant cell. Specifically, for example, a method using *Agrobacterium* or a method in which the expression vector is directly introduced into a plant cell can be used. The method using *Agrobacterium* that can be used is, for example, the method described in Bechtold, E., Ellis, J. and Pelletier, G. (1993) In Planta *Agrobacterium*-mediated gene transfer by infiltration of adult *Arabidopsis* plants. C. R. Acad. Sci. Paris Sci. Vie, 316, 1194-1199 or the method described in Zyprian E, Kado Cl, *Agrobacterium*-mediated plant transformation by novel mini-T vectors in conjunction with a high-copy vir region helper plasmid. Plant Molecular Biology, 1990, 15(2), 245-256.

Examples of the method in which the expression vector is directly introduced into a plant cell that can be used include a microinjection method, an electroporation method (electroporation method), a polyethylene glycol method, a particle gun method, a protoplast fusion method, and a calcium phosphate method.

In addition, when the method in which the flowering-inducing gene is directly introduced into a plant cell is employed, a nucleic acid having a transcription unit such as a promoter nucleotide sequence or a nucleic acid having a transcription terminator nucleotide sequence, which is required for the expression of a flowering-inducing gene of interest, and a flowering-inducing gene of interest are necessary and sufficient, and the vector function is not necessary. Further, even a nucleic acid consisting of the protein coding region of the flowering-inducing gene without having a transcription unit is acceptable as long as it can be integrated into a transcription unit of the host genome, thereby expressing the gene of interest. Even in a case in which the nucleic acid cannot be integrated into the host genome, it is acceptable as long as the flowering-inducing gene is transcribed and/or translated in the cell.

Examples of plant cells into which the expression vector or a flowering-inducing gene of interest without the expression vector is introduced include cells, callus, and suspension culture cells of tissues in plant organs such as flowers, leaves, and roots. The expression vector described herein may be appropriately constructed as a vector suitable for the type of a plant to be produced or it may be constructed as a versatile expression vector and then introduced into a plant cell.

A plant formed with cells into which an expression vector is introduced is not particularly limited. In other words, it is possible to cause slow flowering induction in any plant by introducing the above-described flowering-inducing gene. A target plant is, for example, a flowering plant in some embodiments, and an angiosperm among flowering plants in some other embodiments. Examples of target angiosperms include dicotyledonous plants and monocotyledonous plants such as plants belonging to the families Brassicaceae, Poaceae, Solanaceae, Leguminosae, and Salicaceae (see below), but are not limited to these plants.

Family Brassicaceae: thale-cress (*Arabidopsis thaliana*), lyrate rockcress (*Arabidopsis lyrata*), rapes (*Brassica rapa, Brassica napus, Brassica campestris*), cabbage (*Brassica oleracea* var. *capitata*), napa (*Brassica rapa* var. *pekinensis*), ging-geng-cai (*Brassica rapa* var. *chinensis*), turnip (*Brassica rapa* var. *rapa*), Nozawana (*Brassica rapa* var. *hakabura*), Mizuna (*Brassica rapa* var. *laciniifolia*), Komatsuna (*Brassica rapa* var. *perviridis*), pak choy leaves (*Brassica rapa* var. *chinensis*), radish (*Raphanus sativus*), wasabi or Japanese-horse-radish (*Wasabia japonica*), pink shepherd's-purse (*Capsella rubella*), and the like Family Chenopodiaceae: beet (*Beta vulgaris*)

Family Aceraceae: sugar maple (*Acer saccharum*)

Family Euphorbiaceae: castor bean (*Ricinus communis*)
Family Solanaceae: tobacco (*Nicotiana tabacum*), eggplant (*Solanum melongena*), potato (*Solanum tuberosum*), tomato (*Solanum lycopersicum*), pepper (*Capsicum annuum*), petunia (*Petunia hybrida*), and the like
Family Leguminosae: soybean (*Glycine max*), garden pea (*Pisum sativum*), broad bean (*Vicia faba*), Japanese wisteria (*Wisteria floribunda*), peanut (*Arachis hypogaea*), birdsfoot trefoil (*Lotus japonicus*), kidney bean (*Phaseolus vulgaris*), adzuki bean or English red mung bean (*Vigna angularis*), acacia (*Acacia*), barrelclover (*Medicago truncatula*), chickpea (*Cicer arietinum*), and the like
Family Asteraceae: chrysanthemum (*Chrysanthemum morifolium*), sunflower (*Helianthus annuus*), and the like
Family Arecaceae: oil palm (*Elaeis guineensis, Elaeis oleifera*), coconut palm (*Cocos nucifera*), date palm (*Phoenix dactylifera*), wax palm (*Copernicia*), and the like
Family Anacardiaceae: wax tree (*Rhus succedanea*), cashew tree (*Anacardium occidentale*), lacquer tree (*Toxicodendron vernicifluum*), mango (*Mangifera indica*), pistachio (*Pistacia vera*), and the like
Family Cucurbitaceae: squash (*Cucurbita maxima, Cucurbita moschata, Cucurbita pepo*), cucumber (*Cucumis sativus*), Japanese snake gourd (*Trichosanthes cucumeroides*), bottle gourd (*Lagenaria siceraria* var. *gourda*), and the like
Family Rosaceae: almond (*Amygdalus communis*), rose (*Rosa*), strawberry (*Fragaria vesca*), Japanese cherry (*Prunus*), apple (*Malus pumila* var. *domestica*), peach (*Prunus persica*), and the like
Family Vitaceae: grape (*Vitis vinifera*)
Family Caryophyllaceae: carnation (*Dianthus caryophyllus*) and the like
Family Salicaceae: poplar (*Populus trichocarpa, Populus nigra, Populus tremula*) and the like
Family Poaceae: corn (*Zea mays*), rice (*Oryza sativa*), barley (*Hordeum vulgare*), bread wheat (*Triticum aestivum*), wild einkorn wheat (*Triticum urartu*), Tausch's goatgrass (*Aegilops tauschii*), Purple false brome (*Brachypodium distachyon*), Asian bamboo (*Phyllostachys*), sugarcane (*Saccharum officinarum*), Napier grass (*Pennisetum purpureum*), Erianthus (*Erianthus ravennae*), Japanese silver grass (*Miscanthus virgatum*), sorghum (*Sorghum bicolor*), switch grass (*Panicum*), and the like
Family Liliaceae: tulip (*Tulipa*), lily (*Lilium*), and the like
Of these, plants belonging to the family Poaceae such as sugarcane, corn, Erianthus, rice, sorghum, and bread wheat, and in particular, plants belonging to the genus *Saccharum, Erianthus, Sorghum,* or *Miscanthus* are exemplified in some embodiments.

Other Steps and Methods

After the above-described transformation treatment, a selection step for selecting an appropriate transformant from among plants can be performed by a conventionally known method. The selection method is not particularly limited. For example, selection may be carried out based on drug resistance such as hygromycin resistance. Alternatively, after growing transformants, the flowering induction time of each plant is observed, and then, a plant in which flowering induction occurs earlier than the wild-type plant but later than a transformed plant into which a conventionally known flowering-inducing gene has been introduced may be selected.

In addition, a progeny plant can be produced from a transformed plant obtained by the transformation treatment in accordance with an ordinary method. By selecting a progeny plant maintaining the characteristic that the expression level of the flowering-inducing gene is significantly improved as compared with the wild-type plant based on the flowering induction time, it is possible to produce a plant line which stably maintains the feature of inducing flowering slowly because of the above-described characteristic. It is also possible to obtain a plant-propagating material such as plant cells, seeds, fruits, stock, callus, tuber, cut ears, or mass from a transformed plant or a progeny thereof and produce a stable plant line having the characteristic using such material on a large scale.

As described above, according to the present disclosure, it is possible to cause slow flowering induction to occur by introducing the above-described specific flowering-inducing gene into cells or enhancing the expression of the flowering-inducing gene. In other words, flowering induction can occur in a transformed plant into which the flowering-inducing gene has been introduced or a progeny thereof earlier than the wild-type plant while the flowering induction occurs at a stage when the plant has grown more largely than a transformed plant into which a conventionally known flowering-inducing gene has been introduced. Accordingly, the amount of seeds of the transformed plant into which the flowering-inducing gene has been introduced or a progeny thereof does not decrease due to flowering induction at a stage when the plant is still small.

EXAMPLES

The present disclosure will be described in detail with reference to the Examples below. However, the scope of the present disclosure is not limited to the Examples.

[FT Family Genes in Sugarcane]

In the Examples, a gene (flowering-inducing gene) encoding a florigen defined as a signal substance that induces flower bud formation in sugarcane plants were searched for. FT (FLOWERING LOCUS T) family genes that function as florigen genes have been identified for *Arabidopsis thaliana* and rice (see references listed at the end of the Examples: Kobayashi et al., 1999; Kardailsky et al., 1999; Corbesier et al., 2007; Tamaki et al., 2007; Komiya et al., 2007). However, no FT gene that promotes flowering induction has been identified in sugarcane (Coelho, 2013; Coelho et al., 2014). Therefore, in the Examples, in order to identify florigen genes (flowering-inducing genes) involved in flowering induction in sugarcane, sugarcane FT family genes were searched for in the existing databanks.

In the Examples, NCBI databases (EST, unigene, SRA), SUGARCANE FUNCTIONAL GENOMICS DATABASE (SUCEST-fun), Phytozome, plantGDB, MSU Rice Genome Annotation Project, and the Rice Annotation Project (RAP) were used as databases for obtaining DNA sequence information and amino acid sequence information. In addition, the information on amino acid sequences encoded by candidate FT genes was obtained from a previously published paper on sugarcane (Coelho et al., 2014). In the Examples, DNA and amino acid sequences obtained by performing homology search using the homology search program NCBI BLAST were subjected to lineage analysis using EMBL-EBI Clustal Omega.

Specifically, three amino acid sequences ScFT3 to ScFT5 were obtained from previously published papers disclosing FT genes in sugarcane (Coelho et al., 2013, Coelho et al., 2014). DNA fragment sequences corresponding to these amino acid sequences were obtained from the NCBI databases and SUCEST. In addition to the above, BLAST search was performed using, as queries, information on the sequences of the Hd3a gene (Kojima et al., 2002) and the ZCN8 gene (Meng et al., 2011) known as florigen genes of rice and corn, respectively. As a result, in addition to the information on partial DNA sequences of ScFT3 to SIFTS which were reported with their amino acid sequences in previously conducted studies, partial sequences of five kinds of FT family genes, which are a FT family gene similar to corn ZCN25 and ZCN19 (hereinafter, "ScFT6"), a FT family gene similar to ZCN18 and ZCN24 (hereinafter, "ScFT7"), a FT family gene similar to ZCN8 (hereinafter, "ScZCN8"), a FT family gene similar to ZCN12 (hereinafter, "ScZCN12"), and a FT family gene similar to ZCN16 (hereinafter, "ScZCN16"), were found.

[Primer Designing]

Primers for gene isolation were designed based on the partial sequence information on the above-described FT family genes using Primer3 (software provided by Whitehead Institute for Biomedical Research).

[Plant Material and Cultivation Method]

For cloning of the FT family genes, RNA obtained from the wild-type sugarcane (scientific name: *Saccharum spontaneum* L.; cultivar name: SES 186; the Genebank Project, NARO) was isolated. Leaves, roots, apical buds, and stems of the wild-type sugarcane SES 186 were sampled before and after heading, followed by RNA extraction. Before heading, samples of leaves were collected from each individual which had been cultivated for 17 months under long-day conditions supplemented with natural light (light period of 16 hours, dark period of 8 hours, about 28° C.). Each leaf was taken from the top portion at a level of 30 cm from the tip of the third leaf such that a leaf sample having a length of about 1.5 cm was obtained from one side of the leaf while excluding the costa. After heading, samples of leaves were obtained from both individuals at the early stage of heading when a 1-cm ear came out from the root of a flag leaf of each plant cultivated under short-day conditions without light supplementation and individuals cultivated for 4 weeks after heading. Samples of roots, apical buds, and stems were collected from seedling plants cultivated under long-day conditions (light period of 16 hours, dark period of 8 hours, about 28° C.) after redifferentiation of callus induced from the growth point. A root sample used herein was the white portion of a root including the tip, an apical bud sample used herein was the portion of an apical bud including the uppermost node with a very little portion of a leaf sheath extending from the node, and a stem sample used herein was the portion including the second and third nodes counted from the lowest node of a stem.

[RNA Extraction]

Total RNA was purified from sugarcane samples (leaf: 15-30 mg; root: 20-30 mg; apical bud: about 35 mg; stem: 15-55 mg) using a RNeasy Plant Mini kit (QIAGEN) basically in accordance with the method recommended by the manufacturer. Incorporated genome DNA was removed using a RNase-free DNase set (QIAGEN) basically in accordance with the method recommended by the manufacturer. Thereafter, the amount of RNA was quantitatively determined by NanoDrop ND-1000 (Thermo Fisher Scientific), thereby determining the final concentration.

[Gene Isolation]

cDNA was synthesized using the extracted RNA. cDNA was synthesized basically in accordance with the method recommended by the manufacturer using a PrimeScript RT reagent kit (Takara Bio Inc.) and the extracted RNA (500 ng) as a template. Thereafter, PCR was performed as described below so as to analyze the nucleotide sequence of each amplified DNA fragment.

PCR was performed using PrimeSTAR HS DNA Polymerase (Takara Bio Inc.) as follows: 38 cycles of denaturation at 98° C. for 10 seconds, annealing at 55° C. for 10 seconds, and extension reaction at 72° C. for 1 minute. Further, PCR was performed using ExTaq HS (Takara Bio Inc.) as follows: 40 cycles of denaturation at 94° C. for 30 seconds, annealing at 55° C. for 30 seconds, and extension reaction at 72° C. for 1 minute. PCR products were subjected to agarose gel electrophoresis and the resulting bands were excised and purified. A pENTR/D-TOPO vector (Thermo Fisher Scientific) or poly(A) was added to each fragment amplified by PrimSTAR HS, and then the fragment was subcloned into a pGEM-T Easy vector (Promega), followed by DNA sequence analysis. Each experimental condition followed the instructions of the kits and reagents. For each FT family gene for which full-length sequence information was not obtained by PCR, the full-length sequence was isolated by the Race method and identified. Cloning of the 5' end was performed using a SMARTer RACE 5'/3'Kit (Takara Bio Inc.). Cloning of the 3' end was performed using a 3'-Full RACE Core Set (Takara Bio Inc.).

TABLE 1

| Primer No. | Name of Primer | Amplified gene | Primer Sequence | SEQ ID NO: |
|---|---|---|---|---|
| 1 | attB1_AT1G65480_F | AtFT | ggggacaagtttgtacaaaaaagcaggcttcATGTCTATAAATATAAGAGACCCTCTTAT | 5 |
| 2 | attB2_AT1G65480_R | AtFT | ggggaccactttgtacaagaaagctgggttAAGTCTTCTTCCTCCGCAGCCACTCTCCCT | 6 |
| 3 | ScFT-like-F2 | ScFT3 ScZCN8 | YTIMGIGARTAYYTICAYTGGYTIGT | 7 |
| 4 | ScFT-like-R1 | ScFT3 ScZCN8 | TRAARTTYTGICKCCAICCIGGIGC | 8 |
| 5 | ScFT3-TO-F149 | ScFT3 | CACCCGTCGGTGGCCCATTATTG | 9 |
| 6 | ScFT3-TO-R757 | ScFT3 | TCTTATTTCACCCGGATCGAGT | 10 |
| 7 | attB1_ScZCN8_F | ScZCN8 | ggggacaagtttgtacaaaaaagcaggctccATGTCAGCAACCGATCCTTTGGTCATGGC | 11 |
| 8 | attB2_ScZCN8_R | ScZCN8 | ggggaccactttgtacaagaaagctgggtcCTACTCTTCCCTAAACCTTCTTCCACCCGA | 12 |
| 9 | attB1_ScFT4_F1 | ScFT4 | GGGGACAAGTTTGTACAAAAAAGCAGGCTCCATGGCCGGCAGCGGCAGGGAAAGGGAGAC | 13 |

TABLE 1-continued

| Primer No. | Name of Primer | Amplified gene | Primer Sequence | SEQ ID NO: |
|---|---|---|---|---|
| 10 | attB2_ScFT4_R4 | ScFT4 | GGGGACCACTTTGTACAAGAAAGCTGGGTCTCATGAGTACATCCTCCTTCCCCCGGAGCC | 14 |
| 11 | attB1_ScFT5 | ScFT5 | ggggacaagtttgtacaaaaaagcaggctccATGTTCAATATGTCTAGGGACCCATTGGT | 15 |
| 12 | attB2_ScFT5 | ScFT5 | ggggaccactttgtacaagaaagctgggtcTCACCTTATGTACCTTCTTCCACCACAGCC | 16 |
| 13 | attB_ScZCN12_F1 | ScZCN12 | GGGGACAAGTTTGTACAAAAAAGCAGGCTCCATGTCTCAGGTGGAACCGTTGGTTCTGGT | 17 |
| 14 | attB2_ScZCN12_R4 | ScZCN12 | GGGGACCACTTTGTACAAGAAAGCTGGGTCTTACGAACTTTCGGGCCTGAACCTTCTGCC | 18 |
| 15 | attB1_ScZCN16 | ScZCN16 | ggggacaagtttgtacaaaaaagcaggctccATGTCAAGTGACCCACTTGTTGTAAGCAA | 19 |
| 16 | attB2_ScZCN16 | ScZCN16 | ggggaccactttgtacaagaaagctgggtcTCATCTAATATATCGTCTGCCACCGCACCC | 20 |
| 17 | ScFT6-TO-F13 | ScFT6 | CACCCAAAATTAGCAGTCTTGACTAACC | 21 |
| 18 | ScFT6-TO-R582 | ScFT6 | GCACAGTCAGTGAGATGGTAT | 22 |
| 19 | ScFT7-TO-Met | ScFT7 | CACCATGTCACGAGGCAGGGATCC | 23 |
| 20 | ScFT7_TO_R338 | ScFT7 | TACTGCCTTGACGTCGATGT | 24 |
| 21 | HPTII_semiRT_F | HPTII | CGACGTCTGTCGAGAAGTTTC | 25 |
| 22 | HPTII_semiRT_R | HPTII | ATTCCTTGCGGTCCGAATGG | 26 |

[Preparation of Vector for *Arabidopsis thaliana* Transformation]

Next, a vector used for introducing the above-described FT family genes into *Arabidopsis thaliana* was prepared. Specifically, at first, DNA fragments each containing a full-length coding sequence were obtained by the PCR method described below based on the DNA sequence information obtained by the method described above for the above-described FT family genes. Next, the obtained DNA fragments were separately incorporated into pDONR207 (Thermo Fisher Scientific) or pENTR/D-TOPO (Thermo Fisher Scientific), thereby producing entry clones. Subsequently, each DNA fragment including one coding region was incorporated into a binary vector pDEST_35S_HSP_GWB5 by LR reaction using the entry clone and LR clonase II (Thermo Fisher Scientific), thereby producing a vector for *Arabidopsis thaliana* transformation. The vector for *Arabidopsis thaliana* transformation strongly expresses the corresponding FT family gene constantly under control of the CaMV 35S promoter and the HSP terminator in *Arabidopsis thaliana*.

pDEST_35S_HSP_GWB5 was prepared by cleaving a fragment containing attR4-ccdB-attR2-SRDX of R4pGWB5_SRDX_HSP (Oshima et al., 2011) by restriction enzyme HindIII treatment and inserting a fragment containing 35S-Ω-attR1-ccdB-attR2 obtained by treating pDEST35SHSP (Oshima et al., 2013) with HindIII into the cleavage site.

Hereinafter, detailed procedures for preparing an entry clone for each gene will be described.

<AtFT Gene>

In the Examples, a transformant that overexpresses the FT gene (AtFT gene) from *Arabidopsis thaliana* was prepared for comparison. Prior to preparing a vector for *Arabidopsis thaliana* transformation for introducing the AtFT gene, primers (Primer Nos. 1 and 2) having sequences for adding the attB1 and attB2 sequences were designed based on the nucleotide sequence of the AtFT gene disclosed with NCBI Accession No. NM_105222. An amplified fragment (SEQ ID NO: 27) including the AtFT gene was obtained by PCR using these primers. The obtained amplified fragment was incorporated into pDONR207 (Thermo Fisher Scientific) by BP reaction using BP clonase II (Thermo Fisher Scientific), thereby preparing an entry clone for the AtFT gene.

<OsHd3a Gene>

In the Examples, a transformant that overexpresses the FT gene (OsHd3a gene) from rice was prepared for comparison. Prior to preparing a vector for *Arabidopsis thaliana* transformation for introducing the OsHd3a gene, VectorBuilder Inc. was commissioned to carry out artificial synthesis of a nucleic acid fragment (SEQ ID NO: 28) to which the attB1 sequence was added to the 5' end side of the coding sequence and the attB2 sequence was added to the 3' end side of the same based on the nucleotide sequence of the OsHd3a gene disclosed with NCBI Accession No. AB052944 and incorporation of the fragment into RI201-AN (Takara Bio Inc.). An entry clone was prepared for the OsHd3a gene by BP reaction using the obtained plasmid and pDONR207 (Thermo Fisher Scientific) using BP clonase II (Thermo Fisher Scientific).

<ScFT3 and ScZCN8 Genes>

For the ScFT3 gene and the ScZCN8 gene among the sugarcane-derived FT family genes isolated as described above, a partial fragment was obtained by degenerate PCR using degenerate primers (Primer Nos. 3 and 4), and the full-length sequence was further obtained by degenerate PCR and the Race method. In addition, the ScFT3 gene was cloned into pENTR/D-TOPO (Thermo Fisher Scientific) and the ScZCN8 gene was cloned into pDONR207 (Thermo Fisher Scientific), thereby preparing an entry clone for each of the ScFT3 gene and the ScZCN8 gene.

For the ScFT3 gene, the full-length sequence necessary for entry clone preparation was amplified using Primer Nos. 5 and 6. For the ScZCN8 gene, the full-length sequence necessary for entry clone preparation was amplified using Primer Nos. 7 and 8. The nucleotide sequences of amplified DNA fragments were as follows: ScFT3 gene: SEQ ID NO: 29; and ScZCN8 gene: SEQ ID NO: 30.

<ScFT4, ScFT5, ScFT6, ScFT7, ScZCN12, and ScZCN16 Genes>

For the ScFT4, ScFT5, ScFT6, ScFT7, ScZCN12, and ScZCN16 genes among the sugarcane-derived FT family genes isolated as described above, cloning was performed based on the nucleotide sequence information of the databases, thereby obtaining full-length sequences.

For each of the ScFT4, ScFT5, ScZCN12, and ScZCN16 genes, primers for adding the attB1 sequence to the 5' side of the sequence and the attB2 sequence to the 3' end of the same were designed. Specifically, the following primers were designed: ScFT4 gene: Primer Nos. 9 and 10; ScFT5 gene: Primer Nos. 11 and 12; ScZCN12 gene: Primer Nos. 13 and 14; and ScZCN16 gene: Primer Nos. 15 and 16. The full-length sequences necessary for preparing entry clones each including one of the genes were amplified by PCR using these primers. The nucleotide sequences of amplified DNA fragments were as follows: ScFT4 gene: SEQ ID NO: 31; ScFT5 gene: SEQ ID NO: 32; ScZCN12 gene: SEQ ID NO: 33; and ScZCN16 gene: SEQ ID NO: 34. Each obtained DNA fragment was incorporated into pDONR207 (Thermo Fisher Scientific) by BP reaction, thereby preparing an entry clone for each gene.

Meanwhile, for the ScFT6 gene and the ScFT7 gene, primers in which cacc was added to the 5' side were designed. Specifically, the following primers were designed: ScFT6 gene: Primer Nos. 17 and 18; and ScFT7 gene: Primer Nos. 19 and 20. The full-length sequences necessary for preparing entry clones each including one of the genes were amplified by PCR using these primers. The nucleotide sequences of amplified DNA fragments were as follows: ScFT6 gene: SEQ ID NO: 35; and ScFT7 gene: SEQ ID NO: 36. Each obtained DNA fragment was incorporated into pENTR/D-TOPO (Thermo Fisher Scientific), thereby preparing an entry clone for each of the ScFT6 gene and the ScFT7 gene.

[Functional Evaluation of FT Family Genes in *Arabidopsis thaliana*]

For functional evaluation of the isolated sugarcane-derived FT family genes, transformation of *Arabidopsis thaliana* (*Arabidopsis*) was carried out using the above-described binary vector, thereby analyzing flowering characteristics.

[Transformation Using *Agrobacterium*]

The above-described binary vector plasmid was transformed into *Agrobacterium* (*Agrobacterium tumefaciens*, *Rhizobium radiobacter*) GV3101 by the electroporation method and cultured in an LB medium containing 50 mg/l spectinomycin, 50 mg/l gentamicin, and 50 mg/l rifampicin. Accordingly, *Agrobacterium* transformed with the binary vector was prepared.

[Preparation of *Arabidopsis thaliana* Transformants]

The *Arabidopsis thaliana* FT function-deficient strain ft-10 (Yoo et al. 2005, Kleinboelting et al. 2012) was procured from the *Arabidopsis* Biological Resource Center (ABRC). Basically, the wild-type Col-0 strain and the ft-10 strain of *Arabidopsis thaliana*, each strain forming buds, were transformed by the floral dipping method described in Clough & Bent (1998). In addition, transformation was carried out using *Agrobacterium* including the binary vector pDEST_35S_HSP_GWB5 that had not been subjected to LR reaction, thereby preparing a control. In order to select transformed plants, T1 seeds obtained from the plants treated by the floral dipping method were sterilized and seeded in an MS medium containing 30 mg/l hygromycin and 250 mg/l vancomycin (Murashige and Skoog, 1962, including 0.5% sucrose and 0.8% agar). The medium after seeding was left at 4° C. for 3 days for low-temperature treatment, followed by cultivation at 22° C. under long-day conditions (light period of 16 hours/dark period of 8 hours). On day 15 after the start of cultivation, individuals that survived antibiotics selection were transplanted as transformed plants onto culture soil. Cultivation was continued after transplantation at 22° C. under long-day conditions (light period of 16 hours/dark period of 8 hours).

[Investigation of Flowering Time]

For the investigation of flowering time of T1 plants, transformed *Arabidopsis thaliana* individuals were cultivated at 22° C. under long-day conditions (light period of 16 hours/dark period of 8 hours), and the number of days until flower bud formation was observed and the number of leaves formed by that time (stem leaves and rosette leaves) were counted.

In addition, T2 seeds were collected from the T1 plants cultivated at 22° C. under long-day conditions, and the flowering time under short-day conditions was investigated. It is known that *Arabidopsis thaliana* is less likely to bloom under short-day conditions (light period of 8 hours/dark period of 16 hours, 22° C.). It was therefore expected to easily judge the results of flowering regulation by comparing the results with the results obtained under long-day conditions. Specifically, for the investigation of flowering time of T2 plants under short-day conditions, T2 seeds were allowed to absorb water and low-temperature treated at 4° C. for 3 days and then seeded directly on culture soil. At this time, transformed plants were selected by genomic PCR described below.

[Genomic PCR]

Genome DNA was extracted by a simplified DNA extraction method from rosette leaf pieces of *Arabidopsis thaliana* sampled from early blooming individuals after flowering and the other individuals 30 to 60 days after seeding directly on culture soil. DNA was extracted by disrupting the leaf pieces in extraction buffer (200 mM Tris-HCl (pH 7.5), 250 mM NaCl, 25 mM EDTA), and purifying the centrifuged supernatant by isopropanol precipitation, concentrating the resultant, and suspending the concentrate in TE buffer. The extracted DNA was used as template for PCR. Primers (Primer Nos. 21 and 22) specific to the hygromycin-resistant gene HPTII present on the T-DNA sequence of the binary vector used for transformation and TaKaRa ExTaq (Takara Bio Inc.) were used for carrying out PCR by the method recommended by the manufacturer, and individuals from which amplified fragments were obtained were determined to be transformed plants.

[Measurement of the Amount of Seeds]

The amount of seeds was measured by weighing seeds collected from each of transformed plants dried for about a month after stopping irrigation using a precision balance (Excellence Plus, Metller Toledo).

[Results]

FIG. 1 depicts the results of investigating flowering time by cultivating transformed plants, in which the FT family genes were overexpressed, using the *Arabidopsis thaliana* FT function-deficient strain ft-10 as a host under long-day conditions. As depicted in FIG. 1, for the vector control strain of the FT function-deficient strain ft-10, about 50 true leaves were formed before flower bud formation was observed, and the characteristic that flower bud formation is delayed for a long period of time due to FT function deficiency was confirmed. Meanwhile, flower buds were formed in transformed plants in which the conventionally known AtFT gene or OsHd3a gene was overexpressed when about 5 true leaves were formed, indicating that the FT function was complemented by the introduced gene.

For the ScFT3, ScFT4, SlFT5, ScFT7, ScZCN8, and ScZCN12 genes among the FT family genes isolated in the Examples, it was revealed that the genes function to complement the FT function to induce flower bud formation at a very early stage as with the AtFT gene and the OsHd3a gene as depicted in FIG. 1. Meanwhile, for the ScFT6 and ScZCN16 genes among the FT family genes isolated in the Examples, it was revealed that flower bud formation is induced earlier than that in the vector control strain of the FT function-deficient strain ft-10, while flower bud formation is induced relatively slowly, which is remarkably different from the AtFT gene, the OsHd3a gene, and the other FT family genes isolated in the Examples.

Figure 2:
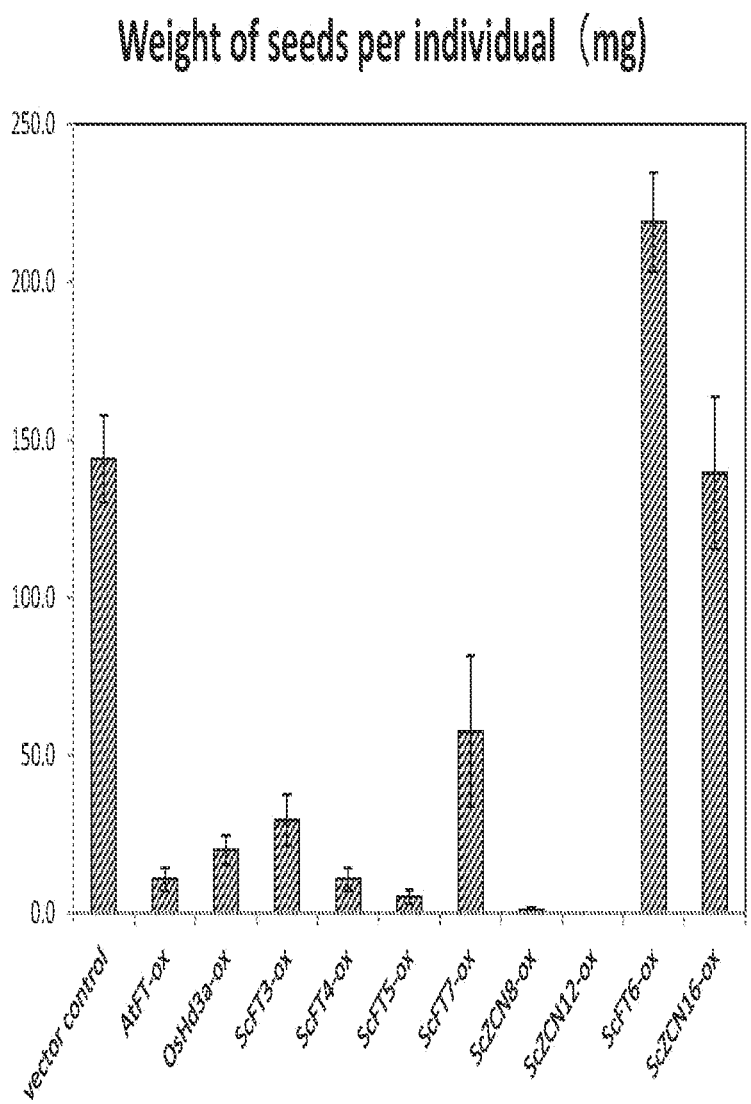
FIG. 2 is a characteristic diagram showing the results of investigating seed yield when transformed plants prepared by separately introducing FT family genes into the FT function-deficient strain were cultivated under long-day conditions.

FIG. 2 depicts the results of measuring the weight of seeds per individual transformed plant for investigating the seed yields of transformed plants cultivated in the same manner. As depicted in FIG. 2, it was found that in the case of introducing the ScFT6 or ScZCN16 gene among the FT family genes isolated in the Examples, the seed yield is remarkably improved compared with the case of introducing any of the AtFT gene, the OsHd3a gene, and the other FT family genes isolated in the Examples. In particular, it was found that in the case of introducing the ScZCN16 gene, the seed yield reaches the level of the vector control strain, and in the case of introducing the ScFT6 gene, the seed yield reaches a level significantly higher than the level of the vector control strain.

As described above, it was shown that in the case of introducing the ScFT6 or ScZCN16 gene among the FT family genes isolated in the Examples, flower bud formation can be induced earlier than that in the vector control strain, and the improved seed yield can be achieved.

Figure 3:
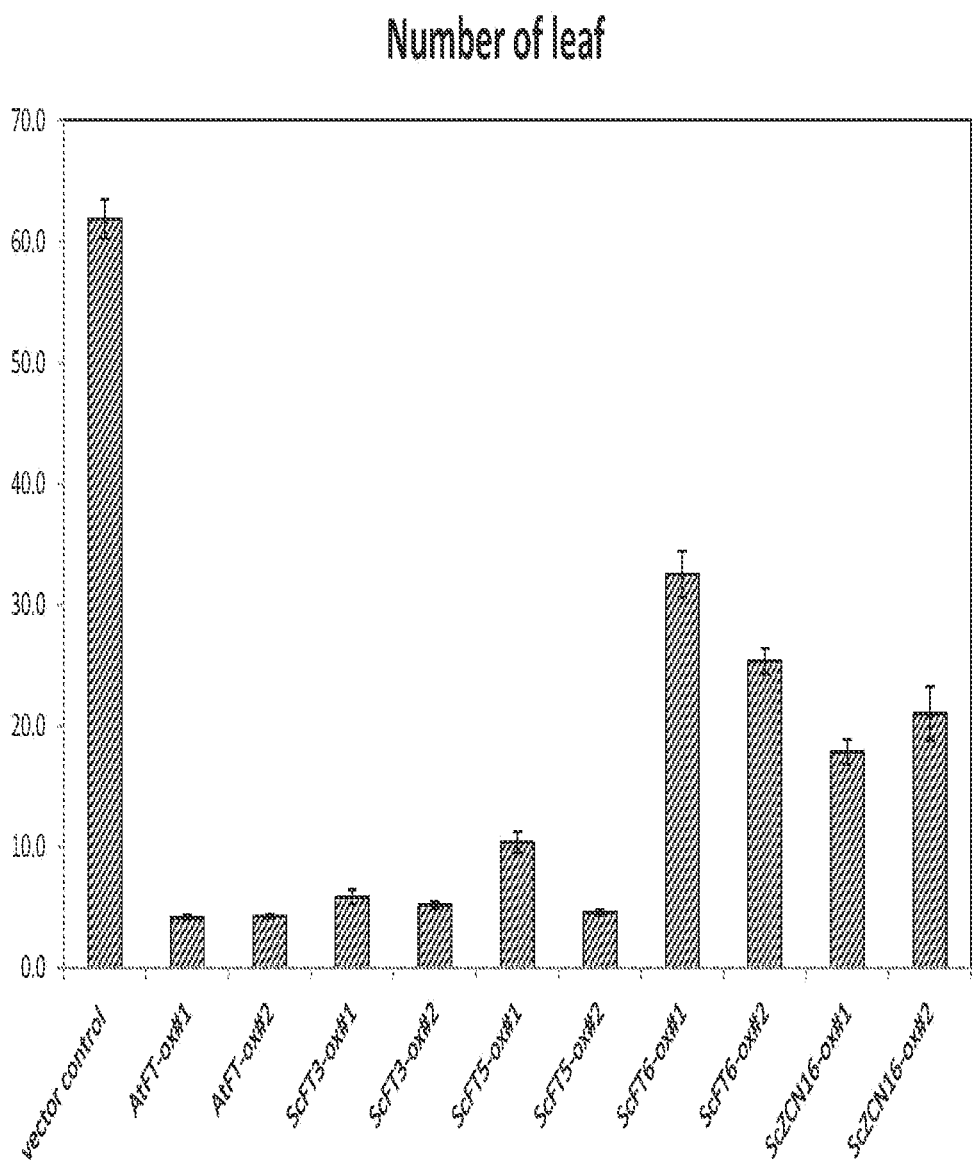
FIG. 3 is a characteristic diagram showing the results of investigating flower bud formation (based on the number of leaves upon flower bud formation) when transformed plants prepared by separately introducing FT family genes into the wild-type strain were cultivated under short-day conditions.
Figure 4:
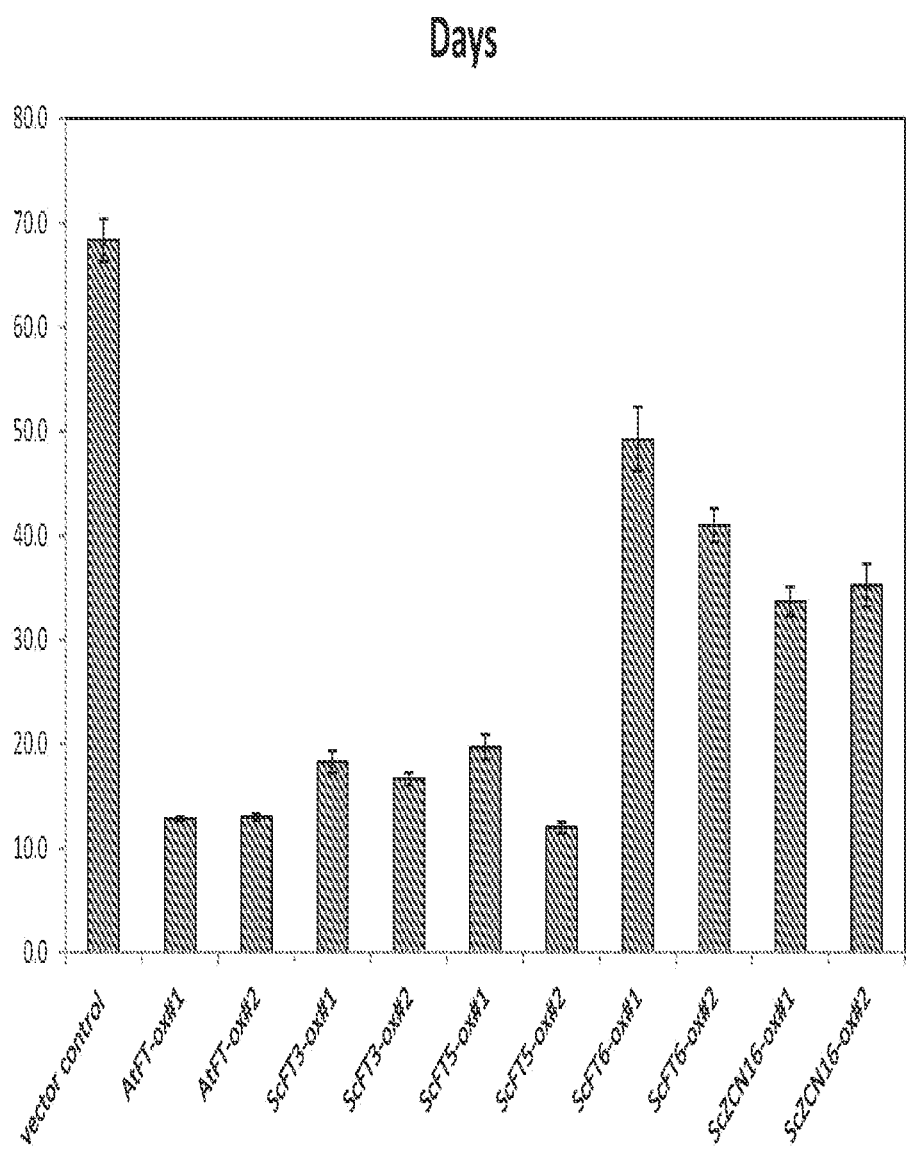
FIG. 4 is a characteristic diagram showing the results of investigating flower bud formation (based on the number of days until flower bud formation) when transformed plants prepared by separately introducing FT family genes into the wild-type strain were cultivated under short-day conditions.

FIGS. 3 and 4 depict the results of investigating flowering time by cultivating transformed plants, in which the FT family genes were overexpressed, using the wild-type *Arabidopsis thaliana* as a host under short-day conditions. The results for two T2 lines (#1 and #2 in the figure) obtained from two different T1 individuals are shown except for the vector control. As depicted in FIGS. 3 and 4, for the vector control strain of the wild-type *Arabidopsis thaliana*, about 60 true leaves were formed before flower bud formation was observed, and the characteristic that flower bud formation is delayed under short-day conditions was confirmed under short-day conditions that are less likely to cause blooming than long-day conditions. Meanwhile, flower buds were formed in transformed plants in which the conventionally known AtFT gene or any FT family gene other than the ScFT6 and ScZCN16 genes was overexpressed when about 5 to 10 true leaves were formed, indicating that flower bud formation is obviously induced by the introduced gene.

On the other hand, it was revealed that flower bud formation is induced earlier in the transformed plants obtained by introducing the ScFT6 or ScZCN16 gene into wild-type *Arabidopsis thaliana* than that in the vector control strain (i.e., the wild-type strain), while flower bud formation is induced relatively slowly, which is remarkably different from transformed plants obtained by introducing the AtFT gene or any other FT family gene.

REFERENCES

Clough S J, Bent A F. (1998) Floral dip: a simplified method for *Agrobacterium*-mediated transformation of *Arabidopsis thaliana*. Plant J. 16(6):735-743.

Coelho C P (2013) MOLECULAR REGULATORY MECHANISM OF FLORAL TRANSITION BY FT/TFL1 ORTHOLOGS AND THE AUTONOMOUSLY EXPRESSED ScID1 MONOCOT-SPECIFIC TRANSCRIPTION FACTOR IN SUGARCANE. Thesis. Universidade Federal de Lavras Coelho C P, Minow M A, Chalfun-Junior A, Colasanti J. (2014) Putative sugarcane FT/TFL1 genes delay flowering time and alter reproductive architecture in *Arabidopsis*. Front Plant Sci. 5:221.

Corbesier L1, Vincent C, Jang S, Fornara F, Fan Q, Searle I, Giakountis A, Farrona S, Gissot L, Turnbull C, Coupland G. (2007) FT protein movement contributes to long-distance signaling in floral induction of *Arabidopsis*. Science. 316(5827): 1030-1033.

Kardailsky I, Shukla V K, Ahn J H, Dagenais N, Christensen S K, Nguyen J T, Chory J, Harrison M J, Weigel D. (1999) Activation tagging of the floral inducer FT. Science. 286(5446):1962-1965.

Kobayashi Y, Kaya H, Goto K, Iwabuchi M, Araki T. (1999) A pair of related genes with antagonistic roles in mediating flowering signals. Science. 286(5446): 1960-1962.

Kojima S, Takahashi Y, Kobayashi Y, Monna L, Sasaki T, Araki T, Yano M. (2002) Hd3a, a rice ortholog of the *Arabidopsis* FT gene, promotes transition to flowering downstream of Hd1 under short-day conditions. Plant Cell Physiol. 43(10): 1096-1105.

Komiya R, Ikegami A, Tamaki S, Yokoi S, Shimamoto K (2008) Hd3a and RFT1 are essential for flowering in rice. Development. 135(4):767-774.

Kleinboelting N, Huep G, Kloetgen A, Viehoever P, Weisshaar B (2012) GABI-Kat Simple Search: new features of the *Arabidopsis thaliana* T-DNA mutant database. Nucleic Acids Res. 40:D1211-D1215.

Meng X, Muszynski M G, Danilevskaya O N. (2011) The FT-like ZCN8 Gene Functions as a Floral Activator and Is Involved in Photoperiod Sensitivity in Maize. Plant Cell. 23(3):942-960.

Murashige T, Skoog F K (1962) A revised medium for rapid growth and bio-assays with tobacco tissue cultures. Physiol. Plant 15 (3): 473-497.

Oshima Y, Mitsuda N, Nakata M, Nakagawa T, Nagaya S, Kato K, Ohme-Takagi M. Novel vector systems to accelerate functional analysis of transcription factors using chimeric repressor gene-silencing technology (CRES-T). (2011) Plant Biotech. 28:201-10.

Oshima Y, Shikata M, Koyama T, Ohtsubo N, Mitsuda N, Ohme-Takagi M. MIXTA-like transcription factors and WAX INDUCER1/SHINE1 coordinately regulate cuticle development in *Arabidopsis* and *Torenia fournieri*. (2013) Plant Cell. 25:1609-24.

Tamaki S, Matsuo S, Wong H L, Yokoi S, Shimamoto K. (2007) Hd3a protein is a mobile flowering signal in rice. Science. 316(5827):1033-1036.

Tsuruta S I, Ebina M, Kobayashi M, Takahashi W. (2017) Complete Chloroplast Genomes of *Erianthus arundinaceus* and *Miscanthus sinensis*: Comparative Genomics and Evolution of the *Saccharum* Complex. PLoS One. 12(1):e0169992.

Yoo S K, Chung K S, Kim J, Lee J H, Hong S M, Yoo S J, Yoo S Y, Lee J S, Ahn J H. (2005) CONSTANS activates SUPPRESSOR OF OVEREXPRESSION OF CONSTANS 1 through FLOWERING LOCUS T to promote flowering in *Arabidopsis*. Plant Physiol. 139(2):770-778.

Wu Z Q, Ge S (2012) The phylogeny of the BEP Glade in grasses revisited: Evidence from the whole-genome sequences of chloroplasts. Mol Phylogenet Evol. 62(1): 573-578.

Sequence Listing

What is claimed is:

1. A transformed plant or transformed plant cell, wherein a flowering-inducing gene encoding the following protein (a) or (b) has been introduced thereinto:
 (a) a protein comprising the amino acid sequence of SEQ ID NO: 2;
 (b) a protein comprising an amino acid sequence having 98% or more identity to the amino acid sequence of SEQ ID NO: 2 and having ability to induce flowering.

2. The transformed plant or transformed plant cell according to claim 1, which belongs to the family Poaceae.

3. The transformed plant or transformed plant cell according to claim 1, which belongs to the genus *Saccharum, Erianthus, Sorghum*, or *Miscanthus*.

4. A flowering induction method, comprising introducing an expression vector comprising a flowering-inducing gene encoding the following protein (a) or (b):
 (a) a protein comprising the amino acid sequence of SEQ ID NO: 2;
 (b) a protein comprising an amino acid sequence having 98% or more identity to the amino acid sequence of SEQ ID NO: 2 and having ability to induce flowering.

5. The flowering induction method according to claim 4, which comprises introducing the flowering-inducing gene into a plant belonging to the family Poaceae.

6. The flowering induction method according to claim 4, which comprises introducing the flowering-inducing gene into a plant belonging to the genus *Saccharum*, Erianthus, Sorghum, or *Miscanthus*.

* * * * *